(12) United States Patent
Cheong et al.

(10) Patent No.: US 9,394,367 B2
(45) Date of Patent: *Jul. 19, 2016

(54) ANTIBODY SPECIFICALLY BINDING TO EPITOPE IN SEMA DOMAIN OF C-MET

(71) Applicant: Samsung Electronics Co., Ltd., Suwon-si, Gyeonggi-do (KR)

(72) Inventors: Kwang-ho Cheong, Cheong (KR); Kyung-ah Kim, Seongnam-si (KR); Seung-hyun Lee, Suwon-si (KR); Ho-yeong Song, Seongnam-si (KR); Yun-jeong Song, Seongnam-si (KR); Young-mi Oh, Seoul (KR); Soo-yeon Jung, Seongnam-si (KR); Mi-young Cho, Seoul (KR)

(73) Assignee: SAMSUNG ELECTRONICS CO., LTD, Suwon-Si (KR)

( * ) Notice: Subject to any disclaimer, the term of this patent is extended or adjusted under 35 U.S.C. 154(b) by 194 days.

This patent is subject to a terminal disclaimer.

(21) Appl. No.: 13/646,523

(22) Filed: Oct. 5, 2012

(65) Prior Publication Data

US 2013/0089557 A1 Apr. 11, 2013

(30) Foreign Application Priority Data

Oct. 5, 2011 (KR) .................. 10-2011-0101292

(51) Int. Cl.
*C07K 16/00* (2006.01)
*A61K 39/395* (2006.01)
*C07K 16/28* (2006.01)
*A61K 39/00* (2006.01)

(52) U.S. Cl.
CPC ....... *C07K 16/2863* (2013.01); *A61K 2039/505* (2013.01); *C07K 2317/24* (2013.01); *C07K 2317/34* (2013.01); *C07K 2317/565* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 5,821,337 | A | * | 10/1998 | Carter et al. ............... 530/387.3 |
| 7,892,550 | B2 | | 2/2011 | Dennis et al. | |
| 2007/0092520 | A1 | | 4/2007 | Dennis et al. | |
| 2009/0324603 | A1 | | 12/2009 | Cao | |
| 2010/0129369 | A1 | * | 5/2010 | Davies et al. ............. 424/138.1 |
| 2011/0104176 | A1 | * | 5/2011 | Cheong et al. ............ 424/152.1 |
| 2011/0129481 | A1 | | 6/2011 | Cheong et al. | |
| 2012/0148607 | A1 | * | 6/2012 | Hultberg et al. .......... 424/174.1 |
| 2013/0089556 | A1 | * | 4/2013 | Cheong et al. ............. 424/138.1 |

FOREIGN PATENT DOCUMENTS

| EP | 2316484 A1 | 5/2011 |
| KR | 1020080000613 A | 1/2008 |
| KR | 1020110074612 A | 3/2012 |
| WO | WO 2009/007427 A2 | 1/2009 |
| WO | WO 2010/037837 A2 | 4/2010 |
| WO | WO 2010/037837 A3 | 4/2010 |
| WO | WO 2010/059654 A1 | 5/2010 |
| WO | WP2013064700 A2 * | 5/2013 |

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Molecular Biomethods Handbook, 2nd Edition, Edited by Walker, 2008, p. 1063.*
Cruse et al., Illustrated Dictionary of Immunology, 1995, p. 76.*
Tiran et al., "A Novel Recombinant Soluble Splice Variant Is a Potent Antagonist of the Hepatocyte Growth Factor/Scatter Factor-Met Pathway," *Clin Cancer Res*, 14:4612-4621 (2008).
Burgess et al., "Fully Human Monoclonal Antibodies to Hepatocyte Growth Factor with Therapeutic Potential against Hepatocyte Growth Fact/c-Met-Dependent Human Tumors," *Cancer Res*, 66: 1721-1729 (2006).
Martens et al., "A Novel One-Armed Anti-c-Met Antibody Inhibits Glioblastoma Growth In vivo," *Clin Cancer Res*,12: 6144-6152 (2006).
International Search Report by the International Searching Authority in International Patent Application No. PCT/KR2012/008069 mailed on Mar. 28, 2013.
Adams et al., "Structural and functional analysis of the interaction between the agonistic monoclonal antibody Apomab and the proapoptotic receptor DR5", *Cell Death and Differentiation*, 15: 751-761 (2008).
European Patent Office, Extended Search Report in European Patent Application No. 12838117.5., May 26, 2015, 5 pp.

* cited by examiner

*Primary Examiner* — Hong Sang
(74) *Attorney, Agent, or Firm* — Leydig, Voit & Mayer, Ltd.

(57) ABSTRACT

An antibody or antigen binding fragment thereof that specifically binds to an epitope in a SEMA domain of c-Met protein, and pharmaceutical compositions, methods, kits, nucleic acids, and cells related thereto.

8 Claims, 15 Drawing Sheets

SEQUENCE LISTING

```
<160> NUMBER OF SEQ ID NOS: 85

<210> SEQ ID NO 1
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: epitope in SEMA domain of c-Met

<400> SEQUENCE: 1

Phe Ser Pro Gln Ile Glu Glu Pro Ser Gln Cys Pro Asp Cys Val Val
1               5                   10                  15

Ser Ala Leu

<210> SEQ ID NO 2
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: epitope in SEMA domain of c-Met

<400> SEQUENCE: 2

Pro Gln Ile Glu Glu Pro Ser Gln Cys Pro
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: epitope in SEMA domain of c-Met

<400> SEQUENCE: 3

Glu Glu Pro Ser Gln
```

```
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: heavy chain CDR1 of AbF46

<400> SEQUENCE: 4

Asp Tyr Tyr Met Ser
1               5

<210> SEQ ID NO 5
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: heavy chain CDR2 of AbF46

<400> SEQUENCE: 5

Phe Ile Arg Asn Lys Ala Asn Gly Tyr Thr Thr Glu Tyr Ser Ala Ser
1               5                   10                  15

Val Lys Gly

<210> SEQ ID NO 6
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: heavy chain CDR3 of AbF46

<400> SEQUENCE: 6

Asp Asn Trp Phe Ala Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: light chain CDR1 of AbF46

<400> SEQUENCE: 7

Lys Ser Ser Gln Ser Leu Leu Ala Ser Gly Asn Gln Asn Asn Tyr Leu
1               5                   10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

<223> OTHER INFORMATION: light chain CDR2 of AbF46

<400> SEQUENCE: 8

Trp Ala Ser Thr Arg Val Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: light chain CDR3 of AbF46

<400> SEQUENCE: 9

Gln Gln Ser Tyr Ser Ala Pro Leu Thr
1               5

<210> SEQ ID NO 10
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: heavy chain variable region of AbF46

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 11
<211> LENGTH: 114
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: light chain variable region of AbF46

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

```
Gly Asn Gln Asn Asn Tyr Leu Ala Trp His Gln Gln Lys Pro Gly Gln
                 35                  40                  45

Pro Pro Lys Met Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gly Gly Thr Lys Val Glu Ile
            100                 105                 110

Lys Arg

<210> SEQ ID NO 12
<211> LENGTH: 1416
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of heavy chain of chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 12
gaattcgccg ccaccatgga atggagctgg gttttttctcg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag gaaaggcact tgagtggttg ggttttatta gaaacaaagc taatggttac     240
acaacagagt acagtgcatc tgtgaagggt cggttcacca tctccagaga taattcccaa     300
agcatcctct atcttcaaat ggacaccctg agagctgagg acagtgccac ttattactgt     360
gcaagagata actggtttgc ttactggggc caagggactc tggtcactgt ctctgcagct     420
agcaccaagg gcccatcggt cttccccctg gcaccctcct ccaagagcac ctctggggc     480 acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
```

```
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga ctcgag                             1416
```

<210> SEQ ID NO 13
<211> LENGTH: 759
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of light chain of chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(90)
<223> OTHER INFORMATION: signal sequence
<220> FEATURE:
<221> NAME/KEY: misc_feature
<222> LOCATION: (91)..(432)
<223> OTHER INFORMATION: VL - light chain variable region
<220> FEATURE:
<221> NAME/KEY: misc_feature
<222> LOCATION: (430)..(435)
<223> OTHER INFORMATION: BsiWI restriction site
<220> FEATURE:
<221> NAME/KEY: misc_feature
<222> LOCATION: (433)..(750)
<223> OTHER INFORMATION: CL - light chain constant region
<220> FEATURE:
<221> NAME/KEY: misc_feature
<222> LOCATION: (751)..(753)
<223> OTHER INFORMATION: stop codon
<220> FEATURE:
<221> NAME/KEY: misc_feature
<222> LOCATION: (754)..(759)
<223> OTHER INFORMATION: XhoI restriction site

<400> SEQUENCE: 13

```
gaattcacta gtgattaatt cgccgccacc atggattcac aggcccaggt cctcatgttg      60
ctgctgctat cggtatctgg tacctgtgga gacattttga tgacccagtc tccatcctcc     120
ctgactgtgt cagcaggaga gaaggtcact atgagctgca agtccagtca gagtctttta     180
gctagtggca accaaaataa ctacttggcc tggcaccagc agaaaccagg acgatctcct     240
aaaatgctga taatttgggc atccactagg gtatctggag tccctgatcg cttcataggc     300
agtggatctg ggacggattt cactctgacc atcaacagtg tgcaggctga agatctggct     360
```

```
gtttattact gtcagcagtc ctacagcgct ccgctcacgt tcggtgctgg gaccaagctg      420
gagctgaaac gtacggtggc tgcaccatct gtcttcatct tcccgccatc tgatgagcag      480
ttgaaatctg gaactgcctc tgttgtgtgc ctgctgaata acttctatcc cagagaggcc      540
aaagtacagt ggaaggtgga taacgccctc caatcgggta actcccagga gagtgtcaca      600
gagcaggaca gcaaggacag cacctacagc ctcagcagca ccctgacgct gagcaaagca      660
gactacgaga aacacaaagt ctacgcctgc gaagtcaccc atcagggcct gagctcgccc      720
gtcacaaaga gcttcaacag gggagagtgt tgactcgag                             759
```

<210> SEQ ID NO 14
<211> LENGTH: 447
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of H1-heavy

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

-continued

```
Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 15
<211> LENGTH: 447
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of H3-heavy

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 16
<211> LENGTH: 447
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of H4-heavy

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80
```

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 17
<211> LENGTH: 220
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of H1-light

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 18
<211> LENGTH: 220
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of H2-light

<400> SEQUENCE: 18

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110

```
Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 19
<211> LENGTH: 220
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of H3-light

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 20
<211> LENGTH: 219
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of H4-light

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215

<210> SEQ ID NO 21
<211> LENGTH: 1350
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of H1-heavy

<400> SEQUENCE: 21
gaggtgcagc tggtggagtc tggggaggc ttggtccagc ctggagggtc cctgagactc      60
tcctgtgcag cctctggatt caccttcact gactactaca tgagctgggt ccgccaggct    120
ccagggaagg ggctggagtg gttgggcttt attagaaaca agctaacgg ttacaccaca     180 gaatacagtg cgtctgtgaa aggcagattc accatctcaa gagataattc aaagaactca    240
ctgtatctgc aaatgaacag cctgaaaacc gaggacacgg ccgtgtatta ctgtgctaga    300
gataactggt tgcttactg ggtcaagga accctggtca ccgtctcctc ggctagcacc     360
aagggcccat cggtcttccc cctggcaccc tcctccaaga gcacctctgg gggcacagcg    420
```

| | |
|---|---:|
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca gagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 22
<211> LENGTH: 1350
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of H3-heavy

<400> SEQUENCE: 22

| | |
|---|---:|
| gaggtgcagc tggtggagtc tgggggaggc ttggtccagc ctggagggtc cctgagactc | 60 |
| tcctgtgcag cctctggatt caccttcact gactactaca tgagctgggt ccgccaggct | 120 |
| ccagggaagg ggctggagtg gttgggcttt attagaaaca aagctaacgg ttacaccaca | 180 |
| gaatacagtg cgtctgtgaa aggcagattc accatctcaa gagataattc aaagaactca | 240 |
| ctgtatctgc aaatgaacag cctgcgtgct gaggacacgg ccgtgtatta ctgtgctaga | 300 |
| gataactggt ttgcttactg gggtcaagga accctggtca ccgtctcctc ggctagcacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |

```
gggcagcccc gagaaccaca ggtgtacacc ctgcccccat cccgggagga gatgaccaag      1080
aaccaggtca gcctgacctg cctggtcaaa ggcttctatc ccagcgacat cgccgtggag      1140
tgggagagca atgggcagcc ggagaacaac tacaagacca cgcctcccgt gctggactcc      1200
gacggctcct tcttcctcta cagcaagctc accgtggaca gagcaggtg gcagcagggg       1260 aacgtcttct catgctccgt gatgcatgag gctctgcaca accactacac gcagaagagc      1320 ctctcccctgt ctccgggtaa atgactcgag                                      1350

<210> SEQ ID NO 23
<211> LENGTH: 1350
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of H4-heavy

<400> SEQUENCE: 23
gaggttcagc tggtggagtc tggcggtggc ctggtgcagc caggggggctc actccgtttg      60 tcctgtgcag cttctggctt caccttcact gattactaca tgagctgggt gcgtcaggcc     120
ccgggtaagg gcctggaatg gttgggtttt attagaaaca aagctaatgg ttacacaaca     180
gagtacagtg catctgtgaa gggtcgtttc actataagca gagataattc caaaaacaca     240
ctgtacctgc agatgaacag cctgcgtgct gaggacactg ccgtctatta ttgtgctaga     300
gataactggt ttgcttactg gggccaaggg actctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660 gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg     1260 aacgtcttct catgctccgt gatgcatgag gctctgcaca accactacac gcagaagagc    1320 ctctcccctgt ctccgggtaa atgactcgag                                    1350

<210> SEQ ID NO 24
<211> LENGTH: 669
<212> TYPE: DNA
<213> ORGANISM: Artificial Sequence
<220> FEATURE:
<223> OTHER INFORMATION: Synthetic
<220> FEATURE:
```

<221> NAME/KEY: misc_feature
<223> OTHER INFORMATION: nucleotide sequence of H1-light

<400> SEQUENCE: 24

| | | | | | |
|---|---|---|---|---|---|
| gacatcgtga | tgacccagtc | tccagactcc | ctggctgtgt | ctctgggcga | gagggccacc | 60 |
| atcaactgca | agtccagcca | gagtctttta | gctagcggga | accaaaataa | ctacttagct | 120 |
| tggcaccagc | agaaaccagg | acagcctcct | aagatgctca | ttatttgggc | atctacccgg | 180 |
| gtatccgggg | tccctgaccg | attcagtggc | agcgggtctg | ggacagattt | cactctcacc | 240 |
| atcagcagcc | tgcaggctga | agatgtggca | gtttattact | gtcagcaatc | ctatagtgct | 300 |
| cctctcacgt | tcggaggcgg | taccaaggtg | gagatcaaac | gtacggtggc | tgcaccatct | 360 |
| gtcttcatct | tcccgccatc | tgatgagcag | ttgaaatctg | gaactgcctc | tgttgtgtgc | 420 |
| ctgctgaata | acttctatcc | cagagaggcc | aaagtacagt | ggaaggtgga | taacgccctc | 480 |
| caatcgggta | actcccagga | gagtgtcaca | gagcaggaca | gcaaggacag | cacctacagc | 540 |
| ctcagcagca | ccctgacgct | gagcaaagca | gactacgaga | aacacaaagt | ctacgcctgc | 600 |
| gaagtcaccc | atcagggcct | gagctcgccc | gtcacaaaga | gcttcaacag | gggagagtgt | 660 |
| tgactcgag | | | | | | 669 |

<210> SEQ ID NO 25
<211> LENGTH: 669
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of H2-light

<400> SEQUENCE: 25

| | | | | | |
|---|---|---|---|---|---|
| gatattgtga | tgacccagac | tccactctcc | ctgcccgtca | cccctggaga | gccggcctcc | 60 |
| atctcctgca | agtccagtca | gagtctttta | gctagtggca | accaaaataa | ctacttggcc | 120 |
| tggcacctgc | agaagccagg | gcagtctcca | cagatgctga | tcatttgggc | atccactagg | 180 |
| gtatctggag | tcccagacag | gttcagtggc | agtgggtcag | gcactgattt | cacactgaaa | 240 |
| atcagcaggg | tggaggctga | ggatgttgga | gtttattact | gccagcagtc | ctacagcgct | 300 |
| ccgctcacgt | tcggacaggg | taccaagctg | gagctcaaac | gtacggtggc | tgcaccatct | 360 |
| gtcttcatct | tcccgccatc | tgatgagcag | ttgaaatctg | gaactgcctc | tgttgtgtgc | 420 |
| ctgctgaata | acttctatcc | cagagaggcc | aaagtacagt | ggaaggtgga | taacgccctc | 480 |
| caatcgggta | actcccagga | gagtgtcaca | gagcaggaca | gcaaggacag | cacctacagc | 540 |
| ctcagcagca | ccctgacgct | gagcaaagca | gactacgaga | aacacaaagt | ctacgcctgc | 600 |
| gaagtcaccc | atcagggcct | gagctcgccc | gtcacaaaga | gcttcaacag | gggagagtgt | 660 |
| tgactcgag | | | | | | 669 |

<210> SEQ ID NO 26
<211> LENGTH: 669
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of H3-light

<400> SEQUENCE: 26

```
gacatcgtga tgacccagtc tccagactcc ctggctgtgt ctctgggcga gagggccacc      60
atcaactgca agtccagcca gagtcttta gctagcggca accaaaataa ctacttagct     120
tggtaccagc agaaaccagg acagcctcct aagctgctca ttatttgggc atctacccgg     180
gtatccgggg tccctgaccg attcagtggc agcgggtctg ggacagattt cactctcacc     240
atcagcagcc tgcaggctga agatgtggca gtttattact gtcagcaatc ctatagtgct     300
cctctcacgt tcggaggcgg taccaaggtg gagatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
tgactcgag                                                             669
```

<210> SEQ ID NO 27
<211> LENGTH: 669
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of H4-light

<400> SEQUENCE: 27

```
gatatccaga tgacccagtc cccgagctcc ctgtccgcct ctgtgggcga tagggtcacc      60
atcacctgca gtccagtca gagtctttta gctagtggca accaaaataa ctacttggcc     120
tggcaccaac agaaaccagg aaaagctccg aaaatgctga ttatttgggc atccactagg     180
gtatctggag tcccttctcg cttctctgga tccgggtctg gacggatttt cactctgacc     240
atcagcagtc tgcagccgga agacttcgca acttattact gtcagcagtc ctacagcgct     300
ccgctcacgt tcggacaggg taccaaggtg gagatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
tgactcgag                                                             669
```

<210> SEQ ID NO 28
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: linker between VH and VL

<400> SEQUENCE: 28

Gly Leu Gly Gly Leu Gly Gly Gly Gly Ser Gly Gly Gly Gly Ser Gly
1               5                   10                  15

Gly Ser Ser Gly Val Gly Ser
            20

<210> SEQ ID NO 29
<211> LENGTH: 1088
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding scFv of huAbF46
      antibody

<400> SEQUENCE: 29

```
gctagcgttt tagcagaagt tcaattggtt gaatctggtg gtggtttggt tcaaccaggt      60
ggttctttga gattgtcttg tgctgcttct ggttttactt tcaccgatta ttacatgtcc     120
tgggttagac aagctccagg taaaggtttg gaatggttgg gtttcattag aaacaaggct     180
aacggttaca ctaccgaata ttctgcttct gttaagggta gattcaccat ttctagagac     240
aactctaaga cacccttgta cttgcaaatg aactccttga gagctgaaga tactgctgtt     300
tattactgcg ctagagataa ttggtttgct tattggggtc aaggtacttt ggttactgtt     360
tcttctggcc tcggggggcct cggaggagga ggtagtggcg gaggaggctc cggtggatcc     420
agcggtgtgg gttccgatat tcaaatgacc caatctccat cttctttgtc tgcttcagtt     480
ggtgatagag ttaccattac ttgtaagtcc tcccaatctt tgttggcttc tggtaatcag     540
aacaattact ggcttggcca tcaacaaaaa ccaggtaaag ctccaaagat gttgattatt     600
tgggcttcta ccagagtttc tggtgttcca tctagatttt ctggttctgg ttccggtact     660
gattttactt tgaccatttc atccttgcaa ccagaagatt tcgctactta ctactgtcaa     720
caatcttact ctgctccatt gacttttggt caaggtacaa aggtcgaaat caagagagaa     780
ttcggtaagc ctatccctaa ccctctcctc ggtctcgatt ctacgggtgg tggtggatct     840
ggtggtggtg gttctggtgg tggtggttct caggaactga caactatatg cgagcaaatc     900
ccctcaccaa ctttagaatc gacgccgtac tctttgtcaa cgactactat tttggccaac     960
gggaaggcaa tgcaaggagt ttttgaatat tacaaatcag taacgtttgt cagtaattgc    1020
ggttctcacc cctcaacaac tagcaaaggc agccccataa acacacagta tgttttttga    1080
gtttaaac                                                             1088
```

<210> SEQ ID NO 30
<211> LENGTH: 5597
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: expression vector including polynucleotide
      encoding scFv of huAbF46 antibody
<220> FEATURE:
<221> NAME/KEY: misc_feature
<222> LOCATION: (573)..(578)
<223> OTHER INFORMATION: NheI restriction site
<220> FEATURE:
<221> NAME/KEY: misc_feature
<222> LOCATION: (588)..(938)
<223> OTHER INFORMATION: huAbF46 VH
<220> FEATURE:
<221> NAME/KEY: misc_feature
<222> LOCATION: (939)..(1007)
<223> OTHER INFORMATION: linker
<220> FEATURE:
<221> NAME/KEY: misc_feature
<222> LOCATION: (1008)..(1349)

```
<223> OTHER INFORMATION: huAbF46 VL
<220> FEATURE:
<221> NAME/KEY: misc_feature
<222> LOCATION: (1350)..(1355)
<223> OTHER INFORMATION: EcoRI restriction site
<220> FEATURE:
<221> NAME/KEY: misc_feature
<222> LOCATION: (1356)..(1397)
<223> OTHER INFORMATION: V5 epitope
<220> FEATURE:
<221> NAME/KEY: misc_feature
<222> LOCATION: (1398)..(1442)
<223> OTHER INFORMATION: (G4S)3 linker
<220> FEATURE:
<221> NAME/KEY: misc_feature
<222> LOCATION: (1443)..(1649)
<223> OTHER INFORMATION: Aga2
<220> FEATURE:
<221> NAME/KEY: misc_feature
<222> LOCATION: (1650)..(1652)
<223> OTHER INFORMATION: TGA(stop codon)
<220> FEATURE:
<221> NAME/KEY: misc_feature
<222> LOCATION: (1653)..(1660)
<223> OTHER INFORMATION: PmeI restriction site

<400> SEQUENCE: 30
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg ttttttcaata ttttctgtta ttgctagcgt tttagcagaa gttcaattgg    600
ttgaatctgg tggtggtttg gttcaaccag gtggttcttt gagattgtct tgtgctgctt    660
ctggttttac tttcaccgat tattacatgt cctgggttag acaagctcca ggtaaaggtt    720
tggaatggtt gggtttcatt agaaacaagg ctaacggtta cactaccgaa tattctgctt    780
ctgttaaggg tagattcacc atttctagag acaactctaa gaacaccttg tacttgcaaa    840
tgaactcctt gagagctgaa gatactgctg tttattactg cgctagagat aattggtttg    900
cttattgggg tcaaggtact ttggttactg tttcttctgg cctcggggc ctcggaggag     960
gaggtagtgg cggaggaggc tccggtggat ccagcggtgt gggttccgat attcaaatga    1020
cccaatctcc atcttctttg tctgcttcag ttggtgatag agttaccatt acttgtaagt    1080
cctcccaatc tttgttggct tctggtaatc agaacaatta cttggcttgg catcaacaaa    1140
aaccaggtaa agctccaaag atgttgatta tttgggcttc taccagagtt tctggtgttc    1200
catctagatt ttctggttct ggttccggta ctgattttac tttgaccatt tcatccttgc    1260
aaccagaaga tttcgctact tactactgtc aacaatctta ctctgctcca ttgacttttg    1320
gtcaaggtac aaaggtcgaa atcaagagag aattcggtaa gcctatccct aaccctctcc    1380
tcggtctcga ttctacgggt ggtggtggat ctggtggtgg tggttctggt ggtggtggtt    1440
ctcaggaact gacaactata tgcgagcaaa tcccctcacc aactttagaa tcgacgccgt    1500
actctttgtc aacgactact attttggcca acggggaaggc aatgcaagga gttttttgaat    1560
```

```
attacaaatc agtaacgttt gtcagtaatt gcggttctca cccctcaaca actagcaaag    1620
gcagccccat aaacacacag tatgtttttt gagtttaaac ccgctgatct gataacaaca    1680
gtgtagatgt aacaaaatcg actttgttcc cactgtactt ttagctcgta caaaatacaa    1740 tatactttc  atttctccgt aaacaacatg ttttcccatg taatatcctt ttctattttt    1800
cgttccgtta ccaactttac acatacttta tatagctatt cacttctata cactaaaaaa    1860
ctaagacaat tttaattttg ctgcctgcca tatttcaatt tgttataaat tcctataatt    1920
tatcctatta gtagctaaaa aaagatgaat gtgaatcgaa tcctaagaga attgggcaag    1980
tgcacaaaca atacttaaat aaatactact cagtaataac ctatttctta gcattttga    2040 cgaaatttgc tattttgtta gagtctttta caccatttgt ctccacacct ccgcttacat    2100
caacaccaat aacgccattt aatctaagcg catcaccaac attttctggc gtcagtccac    2160
cagctaacat aaaatgtaag ctctcggggc tctcttgcct tccaacccag tcagaaatcg    2220
agttccaatc caaaagttca cctgtcccac ctgcttctga atcaaacaag gaataaacg     2280 aatgaggttt ctgtgaagct gcactgagta gtatgttgca gtcttttgga aatacgagtc    2340
ttttaataac tggcaaaccg aggaactctt ggtattcttg ccacgactca tctccgtgca    2400
gttggacgat atcaatgccg taatcattga ccagagccaa aacatcctcc ttaggttgat    2460
tacgaaacac gccaaccaag tatttcggag tgcctgaact attttatat  gcttttacaa    2520 gacttgaaat tttccttgca ataaccgggt caattgttct ctttctattg ggcacacata    2580
taatacccag caagtcagca tcggaatcta gagcacattc tgcggcctct gtgctctgca    2640
agccgcaaac tttcaccaat ggaccagaac tacctgtgaa attaataaca gacatactcc    2700
aagctgcctt tgtgtgctta atcacgtata ctcacgtgct caatagtcac caatgccctc    2760
cctcttggcc ctctcctttt ctttttcga ccgaatttct tgaagacgaa agggcctcgt     2820
gatacgccta ttttatagg ttaatgtcat gataataatg gttcttagg acggatcgct      2880 tgcctgtaac ttacacgcgc ctcgtatctt ttaatgatgg aataatttgg gaatttactc    2940
tgtgtttatt tattttatg ttttgtattt ggattttaga aagtaaataa agaaggtaga     3000
agagttacgg aatgaagaaa aaaaaataaa caaaggttta aaaaatttca acaaaaagcg    3060
tactttacat atatatttat tagacaagaa aagcagatta aatagatata cattcgatta    3120
acgataagta aaatgtaaaa tcacaggatt ttcgtgtgtg gtcttctaca cagacaagat    3180
gaaacaattc ggcattaata cctgagagca ggaagagcaa gataaaaggt agtatttgtt    3240
ggcgatcccc ctagagtctt ttacatcttc ggaaaacaaa aactatttt  tcttaatt      3300 ctttttttac tttctatttt taatttatat atttatatta aaaatttaa attataatta     3360 ttttatagc acgtgatgaa aaggacccag gtggcacttt tcggggaaat gtgcgcggaa     3420
cccctatttg tttattttc taaatacatt caaatatgta tccgctcatg agacaataac     3480
cctgataaat gcttcaataa tattgaaaaa ggaagagtat gagtattcaa catttccgtg    3540
tcgcccttat tccctttttt gcggcatttt gccttcctgt ttttgctcac ccagaaacgc    3600
tggtgaaagt aaaagatgct gaagatcagt tgggtgcacg agtgggttac atcgaactgg    3660
atctcaacag cggtaagatc cttgagagtt ttcgccccga gaacgttttt ccaatgatga    3720 gcactttaa agttctgcta tgtggcgcgg tattatcccg tgttgacgcc gggcaagagc     3780
aactcggtcg ccgcatacac tattctcaga atgacttggt tgagtactca ccagtcacag    3840
aaaagcatct tacggatggc atgacagtaa gagaattatg cagtgctgcc ataaccatga    3900
```

-continued

```
gtgataacac tgcggccaac ttacttctga caacgatcgg aggaccgaag gagctaaccg   3960
cttttttgca caacatgggg gatcatgtaa ctcgccttga tcgttgggaa ccggagctga   4020
atgaagccat accaaacgac gagcgtgaca ccacgatgcc tgtagcaatg gcaacaacgt   4080
tgcgcaaact attaactggc gaactactta ctctagcttc ccggcaacaa ttaatagact   4140
ggatggaggc ggataaagtt gcaggaccac ttctgcgctc ggcccttccg gctggctggt   4200
ttattgctga taaatctgga gccggtgagc gtgggtctcg cggtatcatt gcagcactgg   4260
ggccagatgg taagccctcc cgtatcgtag ttatctacac gacgggcagt caggcaacta   4320
tggatgaacg aaatagacag atcgctgaga taggtgcctc actgattaag cattggtaac   4380
tgtcagacca gtttactcat atatacttta gattgattt aaaacttcat ttttaattta   4440
aaaggatcta ggtgaagatc ctttttgata atctcatgac caaatccct taacgtgagt   4500 tttcgttcca ctgagcgtca gaccccgtag aaaagatcaa aggatcttct tgagatcctt   4560
tttttctgcg cgtaatctgc tgcttgcaaa caaaaaaacc accgctacca gcggtggttt   4620
gtttgccgga tcaagagcta ccaactcttt ttccgaaggt aactggcttc agcagagcgc   4680
agataccaaa tactgtcctt ctagtgtagc cgtagttagg ccaccacttc aagaactctg   4740
tagcaccgcc tacatacctc gctctgctaa tcctgttacc agtggctgct gccagtggcg   4800
ataagtcgtg tcttaccggg ttggactcaa gacgatagtt accggataag gcgcagcggt   4860
cgggctgaac ggggggttcg tgcacacagc ccagcttgga gcgaacgacc tacaccgaac   4920
tgagatacct acagcgtgag cattgagaaa gcgccacgct tcccgaaggg agaaaggcgg   4980
acaggtatcc ggtaagcggc agggtcggaa caggagagcg cacgagggag cttccagggg   5040
ggaacgcctg gtatctttat agtcctgtcg ggtttcgcca cctctgactt gagcgtcgat   5100
ttttgtgatg ctcgtcaggg gggccgagcc tatgaaaaaa cgccagcaac gcggcctttt   5160
tacggttcct ggccttttgc tggccttttg ctcacatgtt ctttcctgcg ttatcccctg   5220
attctgtgga taaccgtatt accgcctttg agtgagctga taccgctcgc cgcagccgaa   5280
cgaccgagcg cagcgagtca gtgagcgagg aagcggaaga gcgcccaata cgcaaaccgc   5340
ctctccccgc gcgttggccg attcattaat gcagctggca cgacaggttt cccgactgga   5400
aagcgggcag tgagcgcaac gcaattaatg tgagttacct cactcattag gcaccccagg   5460
ctttacactt tatgcttccg gctcctatgt tgtgtggaat tgtgagcgga taacaatttc   5520
acacaggaaa cagctatgac catgattacg ccaagctcgg aattaaccct cactaaaggg   5580
aacaaaagct ggctagt                                                 5597
```

<210> SEQ ID NO 31
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-H1 derived from H11-4 clone

<400> SEQUENCE: 31

Pro Glu Tyr Tyr Met Ser
1               5

<210> SEQ ID NO 32
<211> LENGTH: 6
<212> TYPE: PRT
<213> ORGANISM: Artificial Sequence

```
<220> FEATURE:
<223> OTHER INFORMATION: Synthetic
<220> FEATURE:
<221> NAME/KEY: MISC_FEATURE
<223> OTHER INFORMATION: CDR-H1 derived from YC151 clone

<400> SEQUENCE: 32

Pro Asp Tyr Tyr Met Ser
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-H1 derived from YC193 clone

<400> SEQUENCE: 33

Ser Asp Tyr Tyr Met Ser
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-H2 derived from YC244 clone

<400> SEQUENCE: 34

Arg Asn Asn Ala Asn Gly Asn Thr
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-H2 derived from YC321 clone

<400> SEQUENCE: 35

Arg Asn Lys Val Asn Gly Tyr Thr
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-H3 derived from YC354 clone

<400> SEQUENCE: 36

Asp Asn Trp Leu Ser Tyr
1               5

<210> SEQ ID NO 37
<211> LENGTH: 6
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-H3 derived from YC374 clone

<400> SEQUENCE: 37

Asp Asn Trp Leu Thr Tyr
1               5

<210> SEQ ID NO 38
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-L1 derived from L1-1 clone

<400> SEQUENCE: 38

Lys Ser Ser His Ser Leu Leu Ala Ser Gly Asn Gln Asn Asn Tyr Leu
1               5                   10                  15
Ala

<210> SEQ ID NO 39
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-L1 derived from L1-3 clone

<400> SEQUENCE: 39

Lys Ser Ser Arg Ser Leu Leu Ser Ser Gly Asn His Lys Asn Tyr Leu
1               5                   10                  15
Ala

<210> SEQ ID NO 40
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-L1 derived from L1-4 clone

<400> SEQUENCE: 40

Lys Ser Ser Lys Ser Leu Leu Ala Ser Gly Asn Gln Asn Asn Tyr Leu
1               5                   10                  15
Ala

<210> SEQ ID NO 41
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-L1 derived from L1-12 clone

<400> SEQUENCE: 41
```

-continued

```
Lys Ser Ser Arg Ser Leu Leu Ala Ser Gly Asn Gln Asn Asn Tyr Leu
1               5                   10                  15
Ala

<210> SEQ ID NO 42
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-L1 derived from L1-22 clone

<400> SEQUENCE: 42

Lys Ser Ser His Ser Leu Leu Ala Ser Gly Asn Gln Asn Asn Tyr Leu
1               5                   10                  15
Ala

<210> SEQ ID NO 43
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-L2 derived from L2-9 clone

<400> SEQUENCE: 43

Trp Ala Ser Lys Arg Val Ser
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-L2 derived from L2-12 clone

<400> SEQUENCE: 44

Trp Gly Ser Thr Arg Val Ser
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-L2 derived from L2-16 clone

<400> SEQUENCE: 45

Trp Gly Ser Thr Arg Val Pro
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<223> OTHER INFORMATION: CDR-L3 derived from L3-1 clone

<400> SEQUENCE: 46

Gln Gln Ser Tyr Ser Arg Pro Tyr Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-L3 derived from L3-2 clone

<400> SEQUENCE: 47

Gly Gln Ser Tyr Ser Arg Pro Leu Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-L3 derived from L3-3 clone

<400> SEQUENCE: 48

Ala Gln Ser Tyr Ser His Pro Phe Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-L3 derived from L3-5 clone

<400> SEQUENCE: 49

Gln Gln Ser Tyr Ser Arg Pro Phe Thr
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR-L3 derived from L3-32 clone

<400> SEQUENCE: 50

Gln Gln Ser Tyr Ser Lys Pro Phe Thr
1               5

<210> SEQ ID NO 51
<211> LENGTH: 1416
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<223> OTHER INFORMATION: nucleotide sequence of heavy chain of chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 51
gaattcgccg ccaccatgga atggagctgg gtttttctcg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag gaaaggcact tgagtggttg gttttattag aaacaaagc taatggttac     240 acaacagagt acagtgcatc tgtgaagggt cggttcacca tctccagaga taattcccaa     300
agcatcctct atcttcaaat ggacaccctg agagctgagg acagtgccac ttattactgt     360
gcaagagata actggtttgc ttactggggc caagggactc tggtcactgt ctctgcagct     420
agcaccaagg gcccatcggt cttccccctg gcacctcct ccaagagcac ctctgggggc      480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc cccatcccg ggaggagatg     1140 accaagaacc aggtcagcct gacctgcctg gtcaaaggct tctatccag cgacatcgcc    1200 gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
```

```
aagagcctct ccctgtctcc gggtaaatga ctcgag                                   1416
```

<210> SEQ ID NO 52
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: U6-HC7 hinge

<400> SEQUENCE: 52

```
Glu Pro Lys Ser Cys Asp Cys His Cys Pro Pro Cys Pro
1               5                   10
```

<210> SEQ ID NO 53
<211> LENGTH: 435
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding CDR-L3 derived from
     L3-1 clone

<400> SEQUENCE: 53

```
gaattcacta gtgattaatt cgccgccacc atggattcac aggcccaggt cctcatgttg         60
ctgctgctat cggtatctgg tacctgtgga gatatccaga tgacccagtc cccgagctcc        120
ctgtccgcct ctgtgggcga tagggtcacc atcacctgca agtccagtca gagtctttta        180
gctagtggca accaaaataa ctacttggcc tggcaccaac agaaaccagg aaaagctccg        240
aaaatgctga ttatttgggc atccactagg gtatctggag tcccttctcg cttctctgga        300
tccgggtctg gacggattt cactctgacc atcagcagtc tgcagccgga agacttcgca        360
acttattact gtcagcagtc ctacagccgc ccgtacacgt tcggacaggg taccaaggtg        420
gagatcaaac gtacg                                                         435
```

<210> SEQ ID NO 54
<211> LENGTH: 435
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding CDR-L3 derived from
     L3-2 clone

<400> SEQUENCE: 54

```
gaattcacta gtgattaatt cgccgccacc atggattcac aggcccaggt cctcatgttg         60
ctgctgctat cggtatctgg tacctgtgga gatatccaga tgacccagtc cccgagctcc        120
ctgtccgcct ctgtgggcga tagggtcacc atcacctgca agtccagtca gagtctttta        180
gctagtggca accaaaataa ctacttggcc tggcaccaac agaaaccagg aaaagctccg        240
aaaatgctga ttatttgggc atccactagg gtatctggag tcccttctcg cttctctgga        300
tccgggtctg gacggattt cactctgacc atcagcagtc tgcagccgga agacttcgca        360
acttattact gtgggcagtc ctacagccgt ccgctcacgt tcggacaggg taccaaggtg        420
gagatcaaac gtacg                                                         435
```

<210> SEQ ID NO 55
<211> LENGTH: 435
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding CDR-L3 derived from
      L3-3 clone

<400> SEQUENCE: 55
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca gtccagtca gagtctttta   180 gctagtggca accaaaataa ctacttggcc tggcaccaac agaaaccagg aaaagctccg   240
aaaatgctga tatttgggc atccactagg gtatctggag tcccttctcg cttctctgga    300
tccgggtctg gacggattt cactctgacc atcagcagtc tgcagccgga agacttcgca    360
acttattact gtgcacagtc ctacagccat ccgttctctt tcggacaggg taccaaggtg   420
gagatcaaac gtacg                                                    435

<210> SEQ ID NO 56
<211> LENGTH: 435
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding CDR-L3 derived from
      L3-5 clone

<400> SEQUENCE: 56
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca gtccagtca gagtctttta   180 gctagtggca accaaaataa ctacttggcc tggcaccaac agaaaccagg aaaagctccg   240
aaaatgctga tatttgggc atccactagg gtatctggag tcccttctcg cttctctgga    300
tccgggtctg gacggattt cactctgacc atcagcagtc tgcagccgga agacttcgca    360
acttattact gtcagcagtc ctacagccgc ccgtttacgt tcggacaggg taccaaggtg   420
gagatcaaac gtacg                                                    435

<210> SEQ ID NO 57
<211> LENGTH: 4170
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding c-Met protein

<400> SEQUENCE: 57
atgaaggccc ccgctgtgct tgcacctggc atcctcgtgc tcctgtttac cttggtgcag    60
aggagcaatg gggagtgtaa agaggcacta gcaaagtccg agatgaatgt gaatatgaag    120
tatcagcttc ccaacttcac cgcggaaaca cccatccaga tgtcattct acatgagcat   180

```
cacattttcc ttggtgccac taactacatt tatgttttaa atgaggaaga ccttcagaag    240
gttgctgagt acaagactgg gcctgtgctg gaacacccag attgtttccc atgtcaggac    300
tgcagcagca aagccaattt atcaggaggt gtttggaaag ataacatcaa catggctcta    360
gttgtcgaca cctactatga tgatcaactc attagctgtg gcagcgtcaa cagagggacc    420
tgccagcgac atgtctttcc ccacaatcat actgctgaca tacagtcgga ggttcactgc    480
atattctccc cacagataga agagcccagc cagtgtcctg actgtgtggt gagcgccctg    540
ggagccaaag tcctttcatc tgtaaaggac cggttcatca acttctttgt aggcaatacc    600
ataaattctt cttatttccc agatcatcca ttgcattcga tatcagtgag aaggctaaag    660
gaaacgaaag atggttttat gttttttgacg gaccagtcct acattgatgt tttacctgag    720
ttcagagatt cttaccccat taagtatgtc catgcctttg aaagcaacaa ttttatttac    780
ttcttgacgg tccaaaggga aactctagat gctcagactt ttcacacaag aataatcagg    840
ttctgttcca taaactctgg attgcattcc tacatggaaa tgcctctgga gtgtattctc    900
acagaaaaga gaaaaagag atccacaaag aaggaagtgt taatatact tcaggctgcg    960 tatgtcagca agcctggggc ccagcttgct agacaaatag gagccagcct gaatgatgac   1020
attcttttcg gggtgttcgc acaaagcaag ccagattctg ccgaaccaat ggatcgatct   1080
gccatgtgtg cattccctat caaatatgtc aacgacttct tcaacaagat cgtcaacaaa   1140
aacaatgtga gatgtctcca gcattttac ggacccaatc atgagcactg ctttaatagg   1200
acacttctga gaaattcatc aggctgtgaa gcgcgccgtg atgaatatcg aacagagttt   1260
accacagctt tgcagcgcgt tgacttattc atgggtcaat tcagcgaagt cctcttaaca   1320
tctatatcca ccttcattaa aggagacctc accatagcta atcttgggac atcagagggt   1380
cgcttcatgc aggttgtggt ttctcgatca ggaccatcaa cccctcatgt gaattttctc   1440
ctggactccc atccagtgtc tccagaagtg attgtggagc atacattaaa ccaaaatggc   1500
tacacactgg ttatcactgg gaagaagatc acgaagatcc cattgaatgg cttgggctgc   1560
agacatttcc agtcctgcag tcaatgcctc tctgccccac cctttgttca gtgtggctgg   1620
tgccacgaca aatgtgtgcg atcggaggaa tgcctgagcg ggacatggac tcaacagatc   1680
tgtctgcctg caatctacaa ggttttccca aatagtgcac cccttgaagg agggacaagg   1740
ctgaccatat gtgctgggga ctttggattt cggaggaata taaatttga tttaaagaaa   1800 actagagttc tccttggaaa tgagagctgc accttgactt taagtgagag cacgatgaat   1860
acattgaaat gcacagttgg tcctgccatg aataagcatt tcaatatgtc cataattatt   1920
tcaaatggcc acgggacaac acaatacagt acattctcct atgtggatcc tgtaataaca   1980
agtatttcgc cgaaatacgg tcctatggct ggtggcactt tacttacttt aactggaaat   2040
tacctaaaca gtgggaattc tagacacatt tcaattggtg gaaaaacatg tactttaaaa   2100
agtgtgtcaa acagtattct tgaatgttat accccagccc aaaccatttc aactgagttt   2160
gctgttaaat tgaaaattga cttagccaac cgagagacaa gcatcttcag ttaccgtgaa   2220
gatcccattg tctatgaaat tcatccaacc aaatctttta ttagtggtgg gagcacaata   2280
acaggtgttg gaaaaaacct gaattcagtt agtgtcccga gaatggtcat aaatgtgcat   2340
gaagcaggaa ggaactttac agtggcatgt caacatcgct ctaattcaga gataatctgt   2400
tgtaccactc cttccctgca acagctgaat ctgcaactcc cctgaaaac caaagccttt   2460 ttcatgttag atgggatcct ttccaaatac tttgatctca tttatgtaca taatcctgtg   2520
tttaagcctt ttgaaaagcc agtgatgatc tcaatgggca atgaaaatgt actggaaatt   2580
```

```
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcacaggat tgattgctgg tgttgtctca    2820
atatcaacag cactgttatt actacttggg ttttcctgt ggctgaaaaa gagaaagcaa     2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttggacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga atgagagactc ataatccaac tgtaaaagat    3540
cttattggct ttggtcttca agtagccaaa gcatgaaat atcttgcaag caaaaagttt    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacaccttt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctacttatgt gaacgtaaaa    4080
tgtgtcgctc cgtatccttc tctgttgtca tcagaagata cgctgatga tgaggtggac    4140
acacgaccag cctccttctg ggagacatca                                     4170
```

<210> SEQ ID NO 58
<211> LENGTH: 444
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: SEMA domain of c-Met

<400> SEQUENCE: 58

Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
            115                 120                 125

Leu Ser Ser Val Lys Asp Arg Phe Ile Asn Phe Phe Val Gly Asn Thr
130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
            195                 200                 205

Gln Arg Glu Thr Leu Asp Ala Gln Thr Phe His Thr Arg Ile Ile Arg
210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Ile Leu Phe Gly
            275                 280                 285

Val Phe Ala Gln Ser Lys Pro Asp Ser Ala Glu Pro Met Asp Arg Ser
290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
            355                 360                 365

Gln Arg Val Asp Leu Phe Met Gly Gln Phe Ser Glu Val Leu Leu Thr
370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
            435                 440

<210> SEQ ID NO 59
<211> LENGTH: 451
<212> TYPE: PRT
<213> ORGANISM: Artificial Sequence
<220> FEATURE:

<223> OTHER INFORMATION: Synthetic
<220> FEATURE:
<221> NAME/KEY: MISC_FEATURE
<223> OTHER INFORMATION: PSI-IPT domain of c-Met

<400> SEQUENCE: 59

```
Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
            20                  25                  30

Pro Pro Phe Val Gln Cys Gly Trp Cys His Asp Lys Cys Val Arg Ser
            35                  40                  45

Glu Glu Cys Leu Ser Gly Thr Trp Thr Gln Gln Ile Cys Leu Pro Ala
50                  55                  60

Ile Tyr Lys Val Phe Pro Asn Ser Ala Pro Leu Glu Gly Gly Thr Arg
65                  70                  75                  80

Leu Thr Ile Cys Gly Trp Asp Phe Gly Phe Arg Arg Asn Asn Lys Phe
                85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
            115                 120                 125

Ala Met Asn Lys His Phe Asn Met Ser Ile Ile Ser Asn Gly His
130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
            195                 200                 205

Cys Tyr Thr Pro Ala Gln Thr Ile Ser Thr Glu Phe Ala Val Lys Leu
210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
            275                 280                 285

Ser Val Pro Arg Met Val Ile Asn Val His Glu Ala Gly Arg Asn Phe
290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
            355                 360                 365

Ser Met Gly Asn Glu Asn Val Leu Glu Ile Lys Gly Asn Asp Ile Asp
        370                 375                 380
```

```
Pro Glu Ala Val Lys Gly Val Leu Lys Val Gly Asn Lys Ser Cys
385                 390                 395                 400

Glu Asn Ile His Leu His Ser Glu Ala Val Leu Cys Thr Val Pro Asn
            405                 410                 415

Asp Leu Leu Lys Leu Asn Ser Glu Leu Asn Ile Glu Trp Lys Gln Ala
        420                 425                 430

Ile Ser Ser Thr Val Leu Gly Lys Val Ile Val Gln Pro Asp Gln Asn
        435                 440                 445

Phe Thr Gly
    450

<210> SEQ ID NO 60
<211> LENGTH: 313
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: TyrKc domain of c-Met

<400> SEQUENCE: 60

Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45

Thr Glu Gly Ile Ile Met Lys Asp Phe Ser His Pro Asn Val Leu Ser
    50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
                85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
        210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270
```

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310

<210> SEQ ID NO 61
<211> LENGTH: 1332
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynicleotide encoding SEMA domain of c-Met

<400> SEQUENCE: 61

```
ctacatgagc atcacatttt ccttggtgcc actaactaca tttatgtttt aaatgaggaa     60
gaccttcaga aggttgctga gtacaagact gggcctgtgc tggaacaccc agattgtttc    120
ccatgtcagg actgcagcag caaagccaat ttatcaggag gtgtttggaa agataacatc    180
aacatggctc tagttgtcga cacctactat gatgatcaac tcattagctg tggcagcgtc    240
aacagaggga cctgccagcg acatgtcttt ccccacaatc atactgctga catacagtcg    300
gaggttcact gcatattctc cccacagata gaagagccca gccagtgtcc tgactgtgtg    360
gtgagcgccc tgggagccaa agtcctttca tctgtaaagg accggttcat caacttcttt    420
gtaggcaata ccataaattc ttcttatttc ccagatcatc cattgcattc gatatcagtg    480
agaaggctaa aggaacgaa agatggtttt atgttttga cggaccagtc ctacattgat    540
gttttacctg agttcagaga ttcttacccc attaagtatg tccatgcctt tgaaagcaac    600
aattttattt acttcttgac ggtccaaagg gaaactctag atgctcagac ttttcacaca    660
agaataatca ggttctgttc cataaactct ggattgcatt cctacatgga aatgcctctg    720
gagtgtattc tcacagaaaa gagaaaaaag agatccacaa agaaggaagt gtttaatata    780
cttcaggctc gtatgtcag caagcctggg gcccagcttc tagacaaat aggagccagc    840
ctgaatgatg acattctttt cggggtgttc gcacaaagca agccagattc tgccgaacca    900
atggatcgat ctgccatgtg tgcattccct atcaaatatg tcaacgactt cttcaacaag    960
atcgtcaaca aaaacaatgt gagatgtctc cagcattttt acggacccaa tcatgagcac   1020
tgctttaata ggacacttct gagaaattca tcaggctgtg aagcgcgccg tgatgaatat   1080
cgaacagagt ttaccacagc tttgcagcgc gttgacttat tcatgggtca attcagcgaa   1140
gtcctcttaa catctatatc caccttcatt aaaggagacc tcaccatagc taatcttggg   1200
acatcagagg gtcgcttcat gcaggttgtg gtttctcgat caggaccatc aacccctcat   1260
gtgaattttc tcctggactc ccatccagtg tctccagaag tgattgtgga gcatacatta   1320
aaccaaaatg gc                                                        1332
```

<210> SEQ ID NO 62
<211> LENGTH: 1299
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynicleotide encoding PSI-IPT domain of c-Met

<400> SEQUENCE: 62

```
tacacactgg ttatcactgg gaagaagatc acgaagatcc cattgaatgg cttgggctgc    60
agacatttcc agtcctgcag tcaatgcctc tctgccccac cctttgttca gtgtggctgg   120
tgccacgaca aatgtgtgcg atcggaggaa tgcctgagcg ggacatggac tcaacagatc   180
tgtctgcctg caatctacaa ggttttccca aatagtgcac cccttgaagg agggacaagg   240
ctgaccatat gtggctggga ctttggattt cggaggaata taaatttga tttaaagaaa    300
actagagttc tccttggaaa tgagagctgc accttgactt aagtgagag cacgatgaat    360
acattgaaat gcacagttgg tcctgccatg aataagcatt tcaatatgtc cataattatt   420
tcaaatggcc acgggacaac acaatacagt acattctcct atgtggatcc tgtaataaca   480
agtatttcgc cgaaatacgg tcctatggct ggtggcactt tacttacttt aactggaaat   540
tacctaaaca gtgggaattc tagacacatt tcaattggtg gaaaaacatg tactttaaaa   600
agtgtgtcaa acagtattct tgaatgttat accccagccc aaaccatttc aactgagttt   660
gctgttaaat tgaaaattga cttagccaac cgagagacaa gcatcttcag ttaccgtgaa   720
gatcccattg tctatgaaat tcatccaacc aaatctttta ttagtggtgg gagcacaata   780
acaggtgttg ggaaaaacct gaattcagtt agtgtcccga gaatggtcat aaatgtgcat   840
gaagcaggaa ggaactttac agtggcatgt caacatcgct ctaattcaga gataatctgt   900
tgtaccactc cttccctgca acagctgaat ctgcaactcc cctgaaaac caaagccttt    960
ttcatgttag atgggatcct ttccaaatac tttgatctca tttatgtaca taatcctgtg  1020
tttaagcctt ttgaaaagcc agtgatgatc tcaatgggca atgaaaatgt actggaaatt  1080
aagggaaatg atattgaccc tgaagcagtt aaaggtgaag tgttaaaagt tggaaataag  1140
agctgtgaga atatacactt acattctgaa gccgttttat gcacggtccc caatgacctg  1200
ctgaaattga acagcgagct aaatatagag tggaagcaag caatttcttc aaccgtcctt  1260
ggaaaagtaa tagttcaacc agatcagaat ttcacagga                        1299
```

<210> SEQ ID NO 63
<211> LENGTH: 939
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynicleotide encoding TyrKc domain of c-Met

<400> SEQUENCE: 63

```
gtgcatttca atgaagtcat aggaagaggg cattttggtt gtgtatatca tgggactttg    60
ttggacaatg atggcaagaa aattcactgt gctgtgaaat ccttgaacag aatcactgac   120
ataggagaag tttcccaatt tctgaccgag ggaatcatca tgaaagattt tagtcatccc   180
aatgtcctct cgctcctggg aatctgcctg cgaagtgaag ggtctccgct ggtggtccta   240
ccatacatga acatggagag tcttcgaaat tcattcgaa atgagactca taatccaact   300
gtaaaagatc ttattggctt tggtcttcaa gtagccaaag gcatgaaata tcttgcaagc   360
aaaaagtttg tccacagaga cttggctgca agaaactgta tgctggatga aaaattcaca   420
gtcaaggttg ctgattttgg tcttgccaga gacatgtatg ataaagaata ctatagtgta   480
cacaacaaaa caggtgcaaa gctgccagtg aagtggatgg ctttggaaag tctgcaaact   540
caaaagtttta ccaccaagtc agatgtgtgg tcctttggcg tgctcctctg ggagctgatg   600
```

```
acaagaggag cccccacctta tcctgacgta aacacctttg atataactgt ttacttgttg    660
caagggagaa gactcctaca acccgaatac tgcccagacc ccttatatga agtaatgcta    720
aaatgctggc accctaaagc cgaaatgcgc ccatcctttt ctgaactggt gtcccggata    780
tcagcgatct tctctacttt cattggggag cactatgtcc atgtgaacgc tacttatgtg    840
aacgtaaaat gtgtcgctcc gtatccttct ctgttgtcat cagaagataa cgctgatgat    900
gaggtggaca cacgaccagc ctccttctgg gagacatca                           939
```

```
<210> SEQ ID NO 64
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: synthetic polypeptide including core target
      sequence 'EEPSQ'

<400> SEQUENCE: 64

Phe Ala Pro Gln Ile Glu Glu Pro Ser Gln Cys Pro Asp Cys Val Val
1               5                   10                  15

Ser Ala Leu Gly Ala Lys Val Leu
            20
```

```
<210> SEQ ID NO 65
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: synthetic polypeptide including core target
      sequence 'EEPSQ'

<400> SEQUENCE: 65

Cys Ser Pro Gln Ile Glu Glu Pro Ser Gln Cys
1               5                   10
```

```
<210> SEQ ID NO 66
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: synthetic polypeptide including core target
      sequence 'EEPSQ'

<400> SEQUENCE: 66

Cys Pro Gln Ile Glu Glu Pro Ser Gln Ala Cys
1               5                   10
```

```
<210> SEQ ID NO 67
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: synthetic polypeptide including core target
      sequence 'EEPSQ'

<400> SEQUENCE: 67
```

```
Cys Gln Ile Glu Glu Pro Ser Gln Ala Pro Cys
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: synthetic polypeptide including core target
      sequence 'EEPSQ'

<400> SEQUENCE: 68

Cys Ile Glu Glu Pro Ser Gln Ala Pro Asp Cys
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: synthetic polypeptide including core target
      sequence 'EEPSQ'

<400> SEQUENCE: 69

Cys Glu Glu Pro Ser Gln Ala Pro Asp Ala Cys
1               5                   10

<210> SEQ ID NO 70
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: core polypeptide including E168D mutation

<400> SEQUENCE: 70

Glu Asp Pro Ser Gln
1               5

<210> SEQ ID NO 71
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: synthetic polypeptide including core target
      sequence 'EDPSQ'

<400> SEQUENCE: 71

Phe Ser Pro Gln Ile Glu Asp Pro Ser Gln Cys Pro Asp Cys Val Val
1               5                   10                  15

Ser Ala Leu Gly Ala Lys Val Leu
            20

<210> SEQ ID NO 72
<211> LENGTH: 11
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<223> OTHER INFORMATION: synthetic polypeptide including core target
      sequence 'EDPSQ'

<400> SEQUENCE: 72

Cys Ser Pro Gln Ile Glu Asp Pro Ser Gln Cys
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: synthetic polypeptide including core target
      sequence 'EDPSQ'

<400> SEQUENCE: 73

Cys Pro Gln Ile Glu Asp Pro Ser Gln Ala Cys
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: synthetic polypeptide including core target
      sequence 'EDPSQ'

<400> SEQUENCE: 74

Cys Gln Ile Glu Asp Pro Ser Gln Ala Pro Cys
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: synthetic polypeptide including core target
      sequence 'EDPSQ'

<400> SEQUENCE: 75

Cys Ile Glu Asp Pro Ser Gln Ala Pro Asp Cys
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: synthetic polypeptide including core target
      sequence 'EDPSQ'

<400> SEQUENCE: 76

Cys Glu Asp Pro Ser Gln Ala Pro Asp Ala Cys
1               5                   10
```

<210> SEQ ID NO 77
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: mutated epitope in SEMA domain

<400> SEQUENCE: 77

Ala Ala Ala Ala Ala
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: mutated epitope in SEMA domain

<400> SEQUENCE: 78

Ala Glu Pro Ser Gln
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: mutated epitope in SEMA domain

<400> SEQUENCE: 79

Glu Ala Pro Ser Gln
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: mutated epitope in SEMA domain

<400> SEQUENCE: 80

Glu Glu Ala Ser Gln
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: mutated epitope in SEMA domain

<400> SEQUENCE: 81

Glu Glu Pro Ala Gln

<210> SEQ ID NO 82
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: mutated epitope in SEMA domain

<400> SEQUENCE: 82

Glu Glu P

```
Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg

<210> SEQ ID NO 85
<211> LENGTH: 114
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variable Region of Light Chain (VL) for L3-1

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg
```

ANTIBODY SPECIFICALLY BINDING TO EPITOPE IN SEMA DOMAIN OF C-MET

CROSS-REFERENCE TO RELATED APPLICATIONS

This application claims the benefit of Korean Patent Application No. 10-2011-0101292, filed on Oct. 5, 2011, in the Korean Intellectual Property Office, the disclosure of which is incorporated herein in its entirety by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows:—92,434 bytes ASCII (Text) file named "711224_ST25.txt," created Oct. 5, 2012.

BACKGROUND

1. Field

The invention relates to antibody or antigen binding fragment thereof that specifically binds to an epitope in a SEMA domain of c-Met protein, and to pharmaceutical compositions, methods, kits, nucleic acids, and cells related thereto.

2. Description of the Related Art

Hepatocyte growth factor (HGF) is a mesenchyme-derived pleitrophic cytokine that binds the extracellular region of the tyrosine kinase receptor, c-Met, to induce mitogenesis, movement, morphogenesis, and angiogenesis in various normal cells and tumor cells. Regulation of the HGF/c-Met signaling pathway is implicated in various mechanisms related to cancer, such as tumor progression, metastasis, migration, invasion, and angiogenesis. In addition, c-Met amplification or mutation is thought to drive ligand-independent tumorigenesis. Thus, c-Met has recently emerged as a new target for anti-cancer therapy.

In particular, c-Met is known to be involved in induction of resistance to commonly used anti-cancer drugs, and thus, is regarded as an important player in personalized treatments. Representative anti-cancer drugs targeting epidermal growth factor receptor (EGFR) (ERBB1), such as ERBITUX™ (cetuximab) and TARCEVA™ (erlotinib), work by blocking signal transduction related to cancer development. HERCEPTIN™ (trastuzumab), which is a well-known breast cancer drug, targets ERBB2 (HER2) and works by blocking signal transduction necessary for cell proliferation. However, recent findings have indicated that among patients resistant to the drugs described above, anti-cancer drugs do not work due to overexpression of c-Met and activation of other types of signal transduction that leads to cell proliferation. Thus, many pharmaceutical firms are developing anti-cancer drugs to inhibit c-Met.

The related art discloses therapeutic antibody drugs that inhibit the function of c-Met. In this related art, however, antibodies having an original structure induce dimerization of c-Met molecules, thereby causing cancer.

In another related art, which discloses therapeutic antibody drugs that inhibit the function of c-Met, the antibody is capable of inhibiting the binding of c-Met to HGF c-Met, which is a c-Met ligand, but the binding of the antibody to c-Met induces the dimerization of c-Met, independent from the ligand. As a result, the antibody acts as an agonist that induces the transduction of cancer-causing signals.

Another related art discloses, to prevent the dimerization of c-Met, a one-armed antagonistic antibody with respect to c-Met, which is prepared by modifying an agonist, a two-armed antibody, using a genetic recombinant method, and product development in clinical trials is currently under way. However, even in this related art, the antibody works only when the treatment is performed together with chemical therapy, and when the antibody is independently treated, anti-cancer therapeutic effects are proven to be low. Therefore, research into the target on c-Met is needed to develop a novel pharmaceutical composition for preventing or treating cancer that inhibits the function of c-Met.

SUMMARY

Provided is an antibody or antigen binding fragment thereof that specifically binds to an epitope in a SEMA domain of c-Met protein.

Also provided are pharmaceutical compositions for preventing or treating cancer, methods of treating cancer, methods of screening for a c-Met antagonist, kits for diagnosing cancer, nucleic acids encoding the antibody or antigen binding fragment, cells comprising the nucleic acids, and methods for preparing the antibody or antigen binding fragment.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
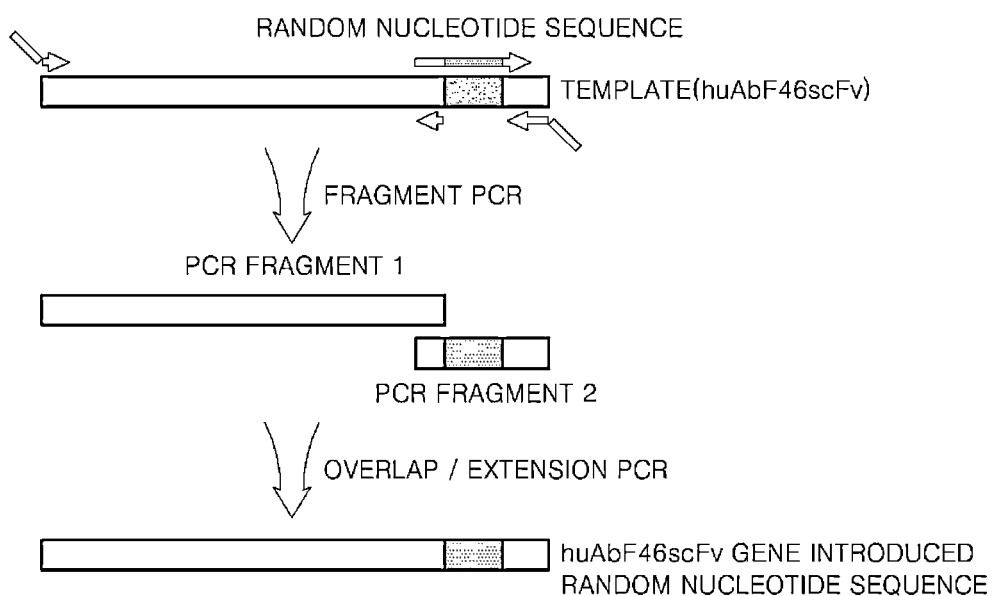
FIG. 1 is a diagram showing the use of overlap extension PCR to obtain an scFv library gene of an huAbF46 antibody in which a desired CDR is mutated.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items According to an embodiment of the present invention, there is provided an antibody or antigen binding fragment thereof that specifically binds to an epitope in a SEMA domain of c-Met protein, wherein the epitope has the amino acid sequence of SEQ ID NO: 1 or a portion thereof.

The term "c-Met" or "c-Met protein" refers to a receptor tyrosine kinase that binds hepatocyte growth factor (HGF). The c-Met protein includes polypeptides encoded by nucleotide sequences identified as GenBank Accession Number NM_000245, proteins encoded by polypeptide sequences identified as GenBank Accession Number NM_000236, or extracellular regions thereof. The receptor tyrosine kinase c-Met participates in various mechanisms, such as cancer development, metastasis, migration, invasion, and angiogenesis.

The HGF receptor, c-Met, has three regions: extracellular, transmembrane, and intracellular. The extracellular region consists of a SEMA domain, which is a HGF-binding domain, with a structure in which a α-subunit is linked by a disulfide bond to a β-subunit, a plexin-semaphorins-integrin (PSI) homology domain, and an immunoglobulin-like fold shared by plexins and transcriptional factors (IPT) domain. In other words, the SEMA domain of c-Met protein exists in the extracellular region of c-Met and corresponds to a HGF-binding region. In particular, the epitope having an amino acid sequence of SEQ ID NO: 1 or a portion thereof corresponds to a loop region between second and third propeller domains among epitopes in the SEMA domain of c-Met protein.

The term "epitope" used herein indicates an antigenic determinant and is interpreted to mean a site on an antigen recognized by an antibody. The epitope may be a polypeptide having an amino acid sequence of SEQ ID NO: 2 or 3. The polypeptide may also be an epitope existing in the SEMA domain of c-Met protein.

The epitope having an amino acid sequence of SEQ ID NO: 2 corresponds to an outermost region of a loop region between second and third propeller domains in the SEMA domain of c-Met protein, and the epitope having an amino acid sequence of SEQ ID NO: 3 refers to a site to which an antibody or an antigen binding fragment thereof most specifically binds.

The antibody or the antigen binding fragment thereof may include a heavy chain variable region including at least one heavy chain complementarity determining region amino acid sequence selected from the group consisting of SEQ ID NO: 4, SEQ ID NO: 5, and SEQ ID NO: 6, and a light chain variable region including at least one light chain complementarity determining region amino acid sequence selected from the group consisting of SEQ ID NO: 7, SEQ ID NO: 8, and SEQ ID NO: 9.

The heavy chain variable region may have an amino acid sequence of SEQ ID NO: 10, and the light chain variable region may have an amino acid sequence of SEQ ID NO: 11.

The antibody or the antigen binding fragment thereof may be an antigen binding fragment selected from the group consisting of monoclonal antibody, bispecific antibody, multispecific antibody, or antigen binding fragment selected from the group consisting of scFv, (scFv)$_2$, Fab, Fab', and F(ab')$_2$.

A naturally occurring intact antibody, or immunoglobulin, includes four polypeptides: two full-length light chains and two full-length heavy chains, in which each light chain is linked to a heavy chain by disulfide bonds. Each heavy chain has a constant region and a variable region. Similarly, each light chain has a constant region and a variable region. There are five heavy chain classes (isotypes): gamma (γ), mu (μ), alpha (α), delta (δ), or epsilon (ε), and additionally several subclasses gamma 1 (γ1), gamma 2 (γ2), gamma 3 (γ3), gamma 4 (γ4), alpha 1 (α1), and alpha 2 (α2). The light chain constant region can be either kappa (κ) or lambda (λ) type. The variable regions differ in sequence among antibodies and are used in the binding and specificity of a given antibody to its particular antigen.

The term "heavy chain" used herein is understood to include a full-length heavy chain including a variable region ($V_H$) having amino acid sequences that determine specificity for antigens and a constant region having three constant domains ($C_{H1}$, $C_{H2}$, and $C_{H3}$), and fragments thereof. In addition, the term "light chain" used herein is understood to include a full-length light chain including a variable region ($V_L$) having amino acid sequences that determine specificity for antigens and a constant region ($C_L$), and fragments thereof.

The term "complementarity determining region (CDR)" used herein refers to an amino acid sequence found in the variable region of a heavy chain or a light chain of an immunoglobulin. The CDRs determine the specificity of an antibody and may provide a contact residue for binding to a specific epitope of an antigen. The heavy chain and the light chain may respectively include three CDRs (CDRH1, CDRH2, and CDRH3, and CDRL1, CDRL2, and CDRL3). Four framework regions, which have more highly conserved amino acid sequences than the CDRs, separate the CDR regions in the $V_H$ or $V_L$.

The term "antigen binding fragment" used herein refers to fragments of an intact immunoglobulin, and any part of a polypeptide including antigen binding regions having the ability to specifically bind to the antigen. For example, the antigen binding fragment may be a F(ab')$_2$ fragment, a Fab' fragment, a Fab fragment, a Fv fragment, or a scFv fragment, but is not limited thereto. A Fab fragment has one antigen binding site and contains the variable regions of a light chain and a heavy chain, the constant region of the light chain, and the first constant region $C_{H1}$ of the heavy chain. A Fab' fragment is different from the Fab fragment in that the Fab' fragment additionally includes the hinge region of the heavy chain, including at least one cysteine residue at the C-terminal of the heavy chain $C_{H1}$ region. The F(ab')$_2$ fragment is produced whereby cysteine residues of the Fab' fragment are joined by a disulfide bond at the hinge region. A Fv fragment is the minimal antibody fragment having only heavy chain variable regions and light chain variable regions, and a recombinant technique for producing the Fv fragment is well known in the art. Two-chain Fv fragments may have a structure in which heavy chain variable regions are linked to light chain variable regions by a non-covalent bond. Single-chain Fv fragments generally may have a dimer structure as in the two-chain Fv fragments in which heavy chain variable regions are covalently bound to light chain variable regions via a peptide linker or heavy and light chain variable regions are directly linked to each other at the C-terminal thereof. The antigen binding fragment may be obtained using a protease (for example, a whole antibody is digested with papain to obtain Fab fragments, and is digested with pepsin to obtain F(ab')$_2$ fragments), and may be prepared by a genetic recombinant technique.

The c-Met may be derived from c-Met selected from the group consisting of a human c-Met, a monkey c-Met, a mouse c-Met, and a rat c-Met.

According to another embodiment of the present invention, there is provided a pharmaceutical composition for preventing or treating cancer, including a therapeutically effective amount of an antibody or antigen binding fragment thereof that specifically binds to an epitope in a SEMA domain of c-Met protein, wherein the epitope has the amino acid sequence of SEQ ID NO: 1 or a portion thereof, and a pharmaceutically acceptable carrier, a diluent, or an excipient.

The cancer may be squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, or head or neck cancers.

The epitope may be a polypeptide having an amino acid sequence of SEQ ID NO: 2 or 3.

The pharmaceutical composition for preventing or treating cancer may include a pharmaceutically acceptable carrier. The pharmaceutically acceptable carrier may be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and/or mineral oil, but is not limited thereto. The pharmaceutical composition may further include a lubricant, a wetting agent, a sweetener, a flavor enhancer, an emulsifying agent, a suspension agent, and/or a preservative.

The pharmaceutical composition for preventing or treating cancer may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestions of protein or peptide, an active ingredient may be coated or formulated in the pharmaceutical composition to prevent digestion. In addition, the pharmaceutical composition may be equipped with a targeting ability to home in on specific cells upon administration.

A suitable dosage of the pharmaceutical composition for preventing or treating cancer may depend on many factors, such as formulation methods, administration methods, ages of patients, body weight, gender, pathologic conditions, diets, administration time, administration route, excretion speed, and reaction sensitivity. A desirable dosage of the pharmaceutical composition may be in the range of about 0.001 to 100 mg/kg for an adult. The term "therapeutically effective amount" used herein refers to a sufficient amount used in preventing or treating cancer or angiogenesis-related diseases.

The pharmaceutical composition may be formulated with a pharmaceutically acceptable carrier and/or an excipient into a unit or a multiple dosage form by a well-known method in the art. In this regard, the formulation may be a solution in oil or an aqueous medium, a suspension, syrup, an emulsifying solution, an extract, powder, granules, a tablet, or a capsule, and may further include a dispersing or a stabilizing agent. In addition, the pharmaceutical composition may be administered as an individual drug, or together with other drugs, and may be administered sequentially or simultaneously with pre-existing drugs. The pharmaceutical composition includes the antibody or the antigen binding fragment thereof, and thus, may be formulated as an immunoliposome. The liposome containing the antibody may be prepared using a well-known method in the art. The immunoliposome is a lipid composition including phosphatidylcholine, cholesterol, and polyethyleneglycol-derived phosphatidylethanolamine, and may be prepared by a reverse phase evaporation method. For example, Fab' fragments may be adhered to the liposome through thiol-disulfide exchange. A chemical drug, such as doxorubicin, may also be included in the liposome.

The antibody or antigen binding fragment may be an antagonist of c-Met protein.

The term "antagonist" is used in the broadest sense herein, and is understood to include all molecules that partially or entirely block, inhibit, and/or neutralize at least one biological activity of a target (for example, c-Met). For example, the term "antagonist antibody" refers to an antibody that inhibits or decreases the biological activity of an antigen, for example c-Met, that the antibody binds. The antagonist may reduce receptor phosphorylation, or inactivate or kill cells that have been activated by a ligand, by binding of a receptor with respect to a ligand. In addition, the antagonist may completely block the interaction between a receptor and a ligand or substantially decrease the interaction therebetween by changing a tertiary structure of the receptor or down-regulating.

In one embodiment, the antibody or the antigen binding fragment thereof may include a heavy chain variable region including at least one heavy chain complementarity determining region amino acid sequence selected from the group consisting of SEQ ID NO: 6, SEQ ID NO: 7, and SEQ ID NO: 8 and a light chain variable region including at least one light chain complementarity determining region amino acid sequence selected from the group consisting of SEQ ID NO: 9, SEQ ID NO: 10, and SEQ ID NO: 11. In addition, the heavy chain variable region may have an amino acid sequence of SEQ ID NO: 12, and the light chain variable region may have an amino acid sequence of SEQ ID NO: 13.

According to another embodiment of the present invention, there is provided a method of treating cancer, the method including administering to a subject a pharmaceutical composition including a therapeutically effective amount of an antibody or antigen binding fragment thereof that specifically binds to an epitope in a SEMA domain of c-Met protein, wherein the epitope has the amino acid sequence of SEQ ID NO: 1 or a portion thereof, and a pharmaceutically acceptable carrier, a diluent, or an excipient.

The pharmaceutical composition for preventing or treating cancer and the administration method are described above.

The subjects to which the pharmaceutical composition for preventing or treating cancer is administered may include animals. For example, the animals may be humans, dogs, cats, or mice.

According to another embodiment of the present invention, there is provided a method of screening a c-Met antagonist, the method including: contacting an epitope in a SEMA domain with a sample to be analyzed, wherein the epitope has the amino acid sequence of SEQ ID NO: 1 or a portion thereof; detecting the binding of the epitope to the sample, wherein, if the epitope and the sample exhibit a binding affinity ranging from about 1 pM to about 10 nM, the sample is a candidate c-Met antagonist.

In the screening method, first, the epitope in the SEMA domain of c-Met protein that has the amino acid sequence of SEQ ID NO: 1 or a portion thereof is contacted with the sample to be analyzed. The c-Met protein may be derived from, but is not limited to, c-Met selected from the group consisting of a human, a monkey, a mouse, and a rat. The term "sample" used herein refers to a certain material used in a screening method to confirm whether the sample binds with the epitope in the SEMA domain of c-Met protein that has the amino acid sequence of SEQ ID NO: 1 or a portion thereof. Examples of the sample include, but are not limited to, polypeptides such as antibodies and antigen binding fragments thereof, chemicals, polynucleotides, antisense-RNA, short hairpin RNA (shRNA), small interference RNA (siRNA), and natural extracts.

Subsequently, a binding affinity between the sample to be analyzed and the epitope in the SEMA domain of c-Met protein that has the amino acid sequence of SEQ ID NO: 1 or a portion thereof is measured. The measurement of binding affinity may be performed using various methods known in the art. For example, the binding affinity may be measured using a Biacore device. In general, a range of the binding affinity that is allowable as a therapeutic drug may be defined such that a binding constant $K_D$ is 10 nM or less. That is, for example, if the binding affinity range is from about 1 pM to about 10 nM, from about 10 pM to about 10 nM, or from about 100 pM to about 10 nM when the binding affinity between the epitope in the SEMA domain of c-Met protein that has the amino acid sequence of SEQ ID NO: 1 or a portion thereof and the sample to be analyzed (e.g., antibody) is measured using a Biacore device by surface plasmon resonance, the sample (e.g., antibody) may be determined as a candidate material for diagnosing, preventing, or treating cancer.

The epitope may be a polypeptide having an amino acid sequence of SEQ ID NO: 2 or 3. In other words, even when the polypeptide having an amino acid sequence of SEQ ID NO: 2 or 3 is used in the screening method instead of the epitope in the SEMA domain of c-Met protein that has the amino acid sequence of SEQ ID NO: 1 or a portion thereof, the same screening results may be obtained.

According to another embodiment of the present invention, there is provided a kit for diagnosing cancer, including the antibody or the antigen binding fragment thereof and other biotechnical tools for various applications using epitope binding of antibodies, antibody fragments, and proteins.

The cancer may be, but is not limited to, lung cancer or ovarian cancer. In some patients with lung cancer or ovarian cancer, it is known that 168$^{th}$ amino acid, that is, Glu in the amino acid sequence of SEQ ID NO: 3 of the epitope in the SEMA domain of c-Met protein is substituted with Asp (M. Sattler et al., *Ther. Adv. Med. Oncol.*, 3(4): 171-184 (2011)).

An antibody or antigen binding fragment that specifically binds to an epitope in a SEMA domain of c-Met protein that has the amino acid sequence of SEQ ID NO: 1, the amino acid sequence of SEQ ID NO: 2, or the amino acid sequence of SEQ ID NO: 3 may be included in a biological sample. For example, the biological sample may be, but is not limited to, a tissue, cell, or whole blood of a suspected cancer patient.

The antibody or antigen binding fragment thereof that specifically binds to an epitope in a SEMA domain of c-Met protein that has the amino acid sequence of SEQ ID NO: 1 or a portion thereof, the amino acid sequence of SEQ ID NO: 2, or the amino acid sequence of SEQ ID NO: 3 has a high binding affinity with the epitope having an amino acid sequence of SEQ ID NO: 3 and a low binding affinity with an epitope (SEQ ID NO: 70) of c-Met protein having the above-described variation. Thus, if a biological sample derived from a suspected cancer patient forms an antigen-antibody complex when contacted with the epitope having an amino acid sequence of SEQ ID NO: 3, but not when contacted with the epitope having an amino acid sequence of SEQ ID NO: 70, the patient may be diagnosed as having cancer.

The formation of the antigen-antibody complex may be confirmed using various detection methods, such as a colormetric method, an electrochemical method, a fluorimetric method, luminometry, a particle counting method, a visual assessment method, or a scintillation counting method.

The term "detection" used herein refers to a process, which is used to detect an antigen-antibody complex, performed using various markers. Examples of the markers include, but are not limited to, an enzyme, a fluorescent material, a ligand, a luminescent material, nanoparticles, and a radioactive isotope.

Examples of the enzyme include acetylcholinesterase, alkaline phosphatase, β-D-galactosidase, horseradish peroxidase, and β-lactamase. Examples of the fluorescent material include fluorescein, $Eu^{3+}$, a $Eu^{3+}$ chelate, and cryptatep. The ligand may be biotin derivatives or the like. The luminescent material may be acridinium ester, isoluminol derivatives, or the like. Examples of the nanoparticles include colloid gold nanoparticles and colored latex nanoparticles. Examples of the radioactive isotope include $^{57}Co$, $^{3}H$, $^{125}I$ and $^{125}I$-Bonton Hunter reagents.

For example, the antigen-antibody complex may be detected using an enzyme-linked immunosorbent assay (ELISA) method. Examples of the ELISA method include direct ELISA using a labeled antibody recognizing an antigen immobilized on a solid support, indirect ELISA using a labeled secondary antibody recognizing a capture antibody in a complex of an antibody recognizing an antigen immobilized on a solid support, direct sandwich ELISA using another labeled antibody recognizing an antigen in an antigen-antibody complex immobilized on a solid support, and indirect sandwich ELISA in which another labeled antibody recognizing an antigen in an antigen-antibody complex immobilized on a solid support is reacted, and then a labeled secondary antibody recognizing the other labeled antibody is used. The antibody or the antigen binding fragment thereof may have a detectable marker. If the antibody or the antigen binding fragment thereof does not have a detectable marker, it may be treated with another antibody capable of capturing the antibody or the antigen binding fragment thereof and having a detectable marker.

According to another embodiment of the present invention, there is provided a nucleic acid encoding an antibody or antigen binding fragment thereof that specifically binds to an epitope in a SEMA domain of c-Met protein, wherein the epitope has the amino acid sequence of SEQ ID NO: 1 or a portion thereof. The nucleic acid encoding the antibody or antigen binding fragment thereof may be, for example, DNA or RNA and may optionally be incorporated in a vector.

According to another embodiment of the present invention, there is provided a cell comprising a nucleic acid encoding an antibody or antigen binding fragment thereof that specifically binds to an epitope in a SEMA domain of c-Met protein, wherein the epitope has the amino acid sequence of SEQ ID NO: 1 or a portion thereof.

According to another embodiment of the present invention, there is provided a method of preparing an antibody or antigen binding fragment thereof that specifically binds to an epitope in a SEMA domain of c-Met protein, wherein the epitope has the amino acid sequence of SEQ ID NO: 1 or a portion thereof, comprising expressing a nucleic acid encoding the antibody or antigen binding fragment thereof in a cell.

One or more embodiments of the present invention will now be described in further detail with reference to the following Examples. However, these examples are for illustrative purposes only and are not intended to limit the scope of the invention.

Example 1

Production of Mouse Antibody AbF46 Against c-Met (1) Immunization of Mice

To obtain immunized mice necessary for developing hybridoma cell lines, 100 μg of human c-Met/Fc fusion protein (R&D Systems) and a complete Freund's adjuvant in the same amount were mixed, and the mixture was administered via an intraperitoneal injection to each of five 4 to 6-week-old BALB/c mice (Japan SLC, Inc.). After two weeks, the antigen (half the previously injected amount) was mixed with an incomplete Freund's adjuvant using the same method as described above, and the mixture was administered to each mouse via an intraperitoneal injection. After one week, final boosting was performed, and blood was collected from the tail of each mouse after three days to obtain serum. Then, serum was diluted at 1/1000 with PBS, and an ELISA was performed to analyze whether the titer of the antibody recognizing c-Met increased. Afterwards, mice in which a sufficient amount of the antibody was obtained were selected, and a cell fusion process was performed on the selected mice.

(2) Cell Fusion and Preparation of the Hybridoma Cells

Three days before a cell fusion experiment, a mixture of 50 μg of PBS and human c-Met/Fc fusion protein was administered via an intraperitoneal injection to each mouse. Each immunized mouse was anesthetized, and its spleen located on the left side of the body was then extracted and ground with a mesh to isolate cells, which were mixed with a culture medium (DMEM) to prepare a spleen cell suspension. The suspension was centrifuged to collect a cell layer. The obtained $1 \times 10^8$ of spleen cells were mixed with $1 \times 10^8$ of myeloma cells (Sp2/0), and the mixture was centrifuged to precipitate the cells. The precipitate was slowly dispersed, treated with 1 ml of 45% polyethylene glycol (PEG) in DMEM, and maintained at 37° C. for one minute before adding 1 ml of DMEM. After introducing additional 10 ml of DMEM for 1 minute, the resultant was maintained in a water bath at 37° C. for 5 minutes. The total amount thereof was made to reach 50 ml, and the resultant was centrifuged. The resulting cell precipitate was re-suspended in an isolation medium (HAT medium) at concentration of $1-2 \times 10^5$ cells/ml. Then, the resultant was distributed to a 96-well plate (0.1 ml per well), which was placed in a carbon dioxide incubator at 37° C. to prepare the hybridoma cells.

(3) Selection of the Hybridoma Cells that Produce Monoclonal Antibodies Against c-Met Protein To select the hybridoma cells that specifically bind to c-Met from the hybridoma cells prepared in (2), the prepared hybridoma cells were screened by an ELISA using as an antigen human c-Met/Fc fusion protein and human Fc protein.

50 ul (2 ug/ml) of human c-Met/Fc fusion protein was coated on each well of a microtiter plate, and unreacted antigens were removed by washing. To exclude antibodies binding to Fc, but not to c-Met, the human Fc protein was coated on each well of a different microtiter plate using the same method as above. Next, 50 ul of hybridoma cell suspension was added to each well of the microtiter plates to react for 1 hour. Then, the microwell plates were washed with phosphate buffer-tween 20 (TBST) solution so as to remove unreacted culture. Goat anti-mouse IgG-horseradish peroxidase (IgG-HRP) was added thereto, and a reaction was allowed to occur at room temperature for 1 hour, and washing was performed with the TBST solution. Subsequently, substrate solution (OPD) of peroxidase was added to each well, and the reaction degree was evaluated by measuring the absorption at 450 nm using an ELISA reader. Through this method, hybridoma cell lines that produce antibodies highly specifically binding to the human c-Met protein and not to the human Fc protein were repeatedly selected. A limiting dilution was performed on the obtained hybridoma cell lines to obtain a single clone of hybridoma cell lines producing monoclonal antibodies. The selected hybridoma cell line producing the monoclonal antibody was registered in the Korean Cell Line Bank with accession number KCLRF-BP-00220 (deposited Oct. 6, 2009 with the Korean Cell Line Research Foundation, Cancer Research Institute, Seoul National University College of Medicine, 28 Yongon-dong, Chongno-Gu, Seoul, 110-744, Korea).

(4) Production and Purification of the Monoclonal Antibody

The hybridoma cells obtained in (3) above were cultured in a serum free medium to produce and purify the monoclonal antibodies from the culture.

First, AbF46 hybridoma cells cultured in 50 ml of culture medium (DMEM) with 10% FBS were centrifuged to obtain cell precipitate, which was washed with 20 ml of PBS more than twice to remove FBS. Then, 50 ml of DMEM was introduced to re-suspend the cell precipitate, and the resultant was incubated in a carbon dioxide incubator at 37° C. for 3 days. After centrifugation to remove antibody-producing cells, cell culture including antibodies was isolated and stored at 4° C., or was used directly. Antibodies were purified from 50 to 300 ml of the culture using a AKTA purification device (GE Health) equipped with an affinity column (protein G agarose column; Pharmacia, USA), and the purified antibodies were stored by replacing the supernatant with PBS using a filter for protein aggregation (Amicon).

Example 2

Preparation of Chimeric Antibody chAbF46 Against c-Met

In general, mouse antibodies are likely to provoke an immune rejection response when administered to humans for the purpose of treatment. To address this problem, from the mouse antibody AbF46 prepared according to Example 1, a chimeric antibody chAbF46, in which a constant region rather than a variable region involved in antigen binding is substituted with a sequence of a human antibody IgG1, was prepared.

A gene having a base sequence corresponding to a heavy chain of 'EcoRI-signal sequence-VH-NheI-CH-TGA-XhoI' (SEQ ID NO: 12) was synthesized and a gene having a base sequence corresponding to a light chain of 'EcoRI-signal sequence-VL-BsiWI-CL-TGA-XhoI' (SEQ ID NO: 13) was synthesized. Afterwards, a fragment of DNA having the base sequence corresponding to a heavy chain (SEQ ID NO: 12) was cloned into pOptiVEC™-TOPO TA Cloning Kit included in OptiCHO™ Antibody Express Kit (Cat no. 12762-019) manufactured by Invitrogen by using a restriction enzyme EcoRI (NEB, R0101S), and a fragment of DNA having the base sequence corresponding to a light chain (SEQ ID NO: 13) was cloned into pcDNA™3.3-TOPO TA Cloning Kit (Cat no. 8300-01) included in OptiCHO™ Antibody Express Kit (Cat no. 12762-019) manufactured by Invitrogen by using a restriction enzyme XhoI (NEB, R0146S), thereby completing construction of vectors for the expression of a chimeric antibody.

Each of the constructed vectors was amplified using Qiagen Maxiprep kit (Cat no. 12662). The vector including the DNA fragment having the heavy chain base sequence and the vector including the DNA fragment having the light chain base sequence were transfected at a ratio of 4:1 (80 ug:20 ug) into $2.5 \times 10^7$ of 293T cells to which 360 ul of 2M $CaCl_2$ was added. Thereafter, the transfected cells were cultured in a DMEM medium including 10% FBS at 37° C. in 5% $CO_2$ for 5 hours, and then cultured in a FBS-free DMEM medium at 37° C. in 5% $CO_2$ for 48 hours.

The cultured cells were centrifuged to obtain 100 ml of a supernatant and the supernatant was purified using AKTA Prime (GE healthcare). A Protein A column (GE healthcare, 17-0405-03) was installed in AKTA Prime, and the culture was flowed therethrough at a flow rate of 5 ml/min and was eluted with IgG elution buffer (Thermo Scientific, 21004). The buffer was exchanged with a PBS buffer, thereby obtaining a finally purified chimeric antibody AbF46 (hereinafter, referred to as chAbF46).

Example 3

Preparation of Humanized Antibody huAbF46 from Chimeric Antibody chAbF46

(1) Heavy Chain Humanization

To design H1-heavy chain and H3-heavy chain, first, a human germline gene that is most homologous to a VH gene of mouse antibody AbF46 was analyzed through NCBI Ig Blast. As a result, VH3-71 was confirmed to have 83% homology at an amino acid level, CDR-H1, CDR-H2, and CDR-H3 of mouse antibody AbF46 were defined by Kabat numbering, and the CDRs of mouse antibody AbF46 were introduced into a framework of the VH3-71 gene. In this regard, $30^{th}$, $48^{th}$, $73^{rd}$ and $78^{th}$ amino acids were back-mutated to the original amino acid sequences of mouse antibody AbF46 (i.e., (S→T), (V→L), (D→N), and (T→L), respectively). Afterwards, $83^{rd}$ and $84^{th}$ amino acids were further mutated (i.e., (R→K) and (A→T), respectively), thereby completing construction of H1-heavy chain (SEQ ID NO: 14) and H3-heavy chain (SEQ ID NO: 15).

To design a H4-heavy chain, a sequence of a human antibody framework was searched. As a result, CDR-H1, CDR-H2, and CDR-H3 of mouse antibody AbF46 having sequences that are closely homologous to a framework sequence of mouse antibody AbF46 and defined by Kabat numbering using an pre-existing VH3 subtype known to be most stable were found and used to construct H4-heavy chain (SEQ ID NO: 16).

(2) Light Chain Humanization

To design H1-light chain (SEQ ID NO: 17) and H2-light chain (SEQ ID NO: 18), first, a human germline gene that is most homologous to a VL gene of mouse antibody AbF46 was analyzed through NCBI Ig Blast. As a result, VK4-1 was confirmed to have 75% homology at an amino acid level, CDR-L1, CDR-L2, and CDR-L3 of mouse antibody AbF46 were defined by Kabat numbering, and the CDRs of mouse antibody AbF46 were introduced into a framework of the VK4-1 gene. In this regard, in the H1-light chain, $36^{th}$, $46^{th}$, and $49^{th}$ amino acids were back-mutated to the original amino acid sequences of mouse antibody AbF46 (i.e., (Y→H), (L→M), and (Y→I), respectively), and, in the H2-light chain, only a $49^{th}$ amino acid was back-mutated (i.e., (Y→I)), thereby completing construction of a H1-light chain and a H2-light chain.

To design H3-light chain (SEQ ID NO: 19), a human germline gene that is most homologous to a VL gene of mouse antibody AbF46 was analyzed through NCBI Blast. As a result, VK2-40 as well as VK4-1 was found. VK2-40 was confirmed to have 61% homology with mouse antibody AbF46 VL at an amino acid level, CDR-L1, CDR-L2, and CDR-L3 of mouse antibody AbF46 were defined by Kabat numbering, and the CDR regions of mouse antibody AbF46 were introduced to a VK4-1 framework. In the H3-light chain, $36^{th}$, $46^{th}$ and $49^{th}$ amino acids were back-mutated (i.e., Y→H, L→M, and Y→I, respectively).

To design the H4-light chain (SEQ ID NO: 20), sequences of a human antibody framework were searched. As a result, CDR-L1, CDR-L2, and CDR-L3 of mouse antibody AbF46 defined by Kabat number using a pre-existing Vk1 subtype known to be the most stable were introduced. In this regard, the H4-light chain was constructed such that $36^{th}$, $46^{th}$ and $49^{th}$ amino acids were further back mutated (i.e., Y→H, L→M, and Y→I, respectively).

Thereafter, a DNA fragment having base sequences corresponding to the heavy chains (H1-heavy: SEQ ID NO: 21, H3-heavy: SEQ ID NO: 22, H4-heavy: SEQ ID NO: 23) was cloned into pOptiVEC™-TOPO TA Cloning Kit included in OptiCHO™ Antibody Express Kit (Cat no. 12762-019) manufactured by Invitrogen by using a restriction enzyme EcoRI (NEB, R0101S), and a DNA fragment having base sequences corresponding to the light chains was cloned into pcDNA™3.3-TOPO TA Cloning Kit included in OptiCHO™ Antibody Express Kit (Cat no. 12762-019) manufactured by Invitrogen by using a restriction enzyme XhoI (NEB, R0146S), thereby completing construction of vectors for the expression of a humanized antibody.

Each of the constructed vectors was amplified using Qiagen Maxiprep kit (Cat no. 12662). The vector including the DNA fragment having the heavy chain base sequences and the vector including the DNA fragment having the light chain base sequences were transfected at a ratio of 4:1 (80 ug:20 ug) into $2.5 \times 10^7$ of 293T cells to which 360 ul of 2M $CaCl_2$ was added. Thereafter, the transfected cells were cultured in a DMEM medium including 10% FBS at 37° C. in 5% $CO_2$ for 5 hours, and then cultured in a FBS-free DMEM medium at 37° C. in 5% $CO_2$ for 48 hours.

The cultured cells were centrifuged to obtain 100 ml of a supernatant and the supernatant was purified using AKTA Prime (GE healthcare). A Protein A column (GE healthcare, 17-0405-03) was installed in AKTA Prime, and the culture was made to flow therethrough at a flow rate of 5 ml/min and was eluted with IgG elution buffer (Thermo Scientific, 21004). The buffer was exchanged with a PBS buffer, thereby obtaining a finally purified humanized antibody AbF46 (hereinafter, referred to as huAbF46). In this regard, the humanized antibody AbF46 used in subsequent Examples included H4-heavy chain and H4-light chain. The variable region of heavy chain (VH) for huAbF46-H4 has an amino acid sequence of 'EVQLVESGGGLVQPGGSLRLSCAASGFTFTDYYMSWVRQAPGKGLEWLGFIRNKAN GYTTEYSASVKGRFTISRDNSKNTLYLQMNSL-RAEDTAVYYCARDNWFAYVVGQGTLV TVSS' (SEQ ID NO: 83) and the variable region of light chain (VL) for huAbF46-H4 has an amino acid sequence of 'DIQMTQSPSSLSASVGDRVTITCKSSQS-LLASGNQNNYLAWHQQKPGKAPKMLIIWAS TRVS-GVPSRFSGSGSGTDFTLTISSLQPEDFA-TYYCQQSYSAPLTFGQGTKVEIKR' (SEQ ID NO: 84).

Example 4

Selection of Affinity Maturated Ab from huAbF46 Antibody and Identification of Binding Affinity Thereof (1) Preparation of scFv Library of the huAbF46 Antibody Genes for preparing scFv of the huAbF46 antibody were designed by using the heavy chain variable region and light chain variable region of the huAbF46 antibody. Each of the heavy chain variable region and light chain variable region was designed to have a 'VH-linker-VL' form, in which the linker was designed to have an amino acid sequence of 'GLGGLGGGGSGGGGSGGSSGVGS' (SEQ ID NO: 28). A polynucleotide (SEQ ID NO: 29) encoding scFv of huAbF46 antibody designed as described above was synthesized (Bioneer, Inc.), and a vector for expressing the polynucleotide was represented as SEQ ID NO: 30. Then, resultants expressed by the vector were analyzed, and c-Met specific binding was identified.

(2) Preparation of Gene Library for Affinity Maturation

1) Selection of Target CDR and Preparation of Primer

For affinity maturation of the huAbF46 antibody, 6 complementarity determining regions (CDRs) were defined by 'Kabat numbering' from the prepared mouse antibody AbF46. CDRs are shown in Table 1.

TABLE 1

| | CDR1 | CDR2 | CDR3 |
|---|---|---|---|
| AbF46 heavy chain CDR amino acid sequence | DYYMS (SEQ ID NO: 4) | FIRNKANGYTTEYS ASVKG (SEQ ID NO: 5) | DNWFAY (SEQ ID NO: 6) |
| AbF46 light chain CDR amino acid sequence | KSSQSLLASGN QNNYLA (SEQ ID NO: 7) | WASTRVS (SEQ ID NO: 8) | QQSYSAPLT (SEQ ID NO: 9) |

Primers were prepared as follows in order to randomly introduce sequences of target CDR. According to existing methods of randomly introducing sequences, N codon was used such that any base could be introduced into sites to be mutated at the same rate (25% A, 25% G, 25% C, and 25% T). However, according to the current embodiment, in order to randomly introduce bases into CDRs of the huAbF46 antibody, 85% of the first and second nucleotides were preserved among three wild-type nucleotides coding amino acids of each CDR, and 5% of each of the other three bases was introduced. In addition, the primer was designed such that the three bases could be introduced into the third nucleotide (33% G, 33% C, and 33% T).

2) Preparation of huAbF46 Antibody Libraries and Identification of Binding Force to c-Met The construction of an antibody gene library was performed using the primers prepared in operation (1) described above. A polynucleotide encoding scFv of the huAbF46 antibody was used as a template. Two PCR fragments were prepared as shown in FIG. 1 and libraries for each of the 6 CDRs were constructed by using an overlap extension PCR.

The binding forces of the wild-type antibody (scFv of huAbF46) and library antibodies to c-Met were identified. While the binding force of most library antibodies to c-Met was lower than that of the wild-type antibody, mutants in which the binding force to c-Met was not reduced were identified.

(3) Selection of Antibodies with Improved Affinity from the Library

Library antibodies having an improved c-Met binding force were sequenced. The obtained sequences are shown in Table 2 below and were transformed into IgG. Among the clones below, 4 types of antibodies produced from L3-1, L3-2, L3-3, and L3-5 were selected and subsequent experiments were performed using these antibodies. The variable region of light chain (VL) for antibody produced from L3-1 has an amino acid sequence of (SEQ ID NO: 85)
'DIQMTQSPSSLSASVGDRVTITCKSSQSLLASGNQNNYLAWHQQKPGKA

PKMLIIWASTRVSGVPSRFSGSGSGTDFTLTISSLQPEDFATYYCQQSYS

RPYTFGQGTKVEIKR'.

TABLE 2

| Name of clone | Library | CDR sequence |
|---|---|---|
| H11-4 | CDR-H1 | PEYYMS (SEQ ID NO: 31) |
| YC151 | CDR-H1 | PDYYMS (SEQ ID NO: 32) |
| YC193 | CDR-H1 | SDYYMS (SEQ ID NO: 33) |
| YC244 | CDR-H2 | RNNANGNT (SEQ ID NO: 34) |
| YC321 | CDR-H2 | RNKVNGYT (SEQ ID NO: 35) |
| YC354 | CDR-H3 | DNWLSY (SEQ ID NO: 36) |
| YC374 | CDR-H3 | DNWLTY (SEQ ID NO: 37) |
| L1-1 | CDR-L1 | KSSHSLLASGNQNNYLA (SEQ ID NO: 38) |
| L1-3 | CDR-L1 | KSSRSLLSSGNHKNYLA (SEQ ID NO: 39) |
| L1-4 | CDR-L1 | KSSKSLLASGNQNNYLA (SEQ ID NO: 40) |
| L1-12 | CDR-L1 | KSSRSLLASGNQNNYLA (SEQ ID NO: 41) |

TABLE 2-continued

| Name of clone | Library | CDR sequence |
|---|---|---|
| L1-22 | CDR-L1 | KSSHSLLASGNQNNYLA (SEQ ID NO: 42) |
| L2-9 | CDR-L2 | WASKRVS (SEQ ID NO: 43) |
| L2-12 | CDR-L2 | WGSTRVS (SEQ ID NO: 44) |
| L2-16 | CDR-L2 | WGSTRVP (SEQ ID NO: 45) |
| L3-1 | CDR-L3 | QQSYSRPYT (SEQ ID NO: 46) |
| L3-2 | CDR-L3 | GQSYSRPLT (SEQ ID NO: 47) |
| L3-3 | CDR-L3 | AQSYSHPFS (SEQ ID NO: 48) |
| L3-5 | CDR-L3 | QQSYSRPFT (SEQ ID NO: 49) |
| L3-32 | CDR-L3 | QQSYSKPFT (SEQ ID NO: 50) |

(4) Transformation of Selected Antibodies to IgG

A polynucleotide encoding the heavy chain of the selected 4 types of antibodies (L3-1, L3-2, L3-3, and L3-5) consisted of 'EcoRI-signal sequence-VH-NheI-CH-XhoI' (SEQ ID NO: 51), and amino acids of the heavy chain were not modified after affinity maturation, and thus the heavy chain of the huAbF46 antibody was used. However, the hinge region was replaced with a U6-HC7 hinge region (SEQ ID NO: 52), not with the hinge region of human IgG1. A gene of the light chain was designed to have 'EcoRI-signal sequence-VL-BsiWI-CL-XhoI', and polynucleotides (SEQ ID NOs: 53 to 56) encoding light chain variable regions of the selected 4 types of antibodies after affinity maturation were synthesized by Bioneer, Inc. Then, vectors for expression of antibodies having improved affinity were constructed by cloning a DNA fragment (SEQ ID NO: 51) having the sequence corresponding to the heavy chain in a pOptiVEC™-TOPO TA Cloning Kit included in an OptiCHO™ Antibody Express Kit (Cat No. 12762-019) manufactured by Invitrogen and DNA fragments (a DNA fragment including L3-1-derived CDR-L3 (SEQ ID NO: 53), a DNA fragment including L3-2-derived CDR-L3 (SEQ ID NO: 54), a DNA fragment including L3-3-derived CDR-L3 (SEQ ID NO: 55), and a DNA fragment including L3-5-derived CDR-L3 (SEQ ID NO: 56)) corresponding to the light chain in a pcDNA™3.3-TOPO TA Cloning Kit (Cat No. 8300-01) by using a restriction enzyme, EcoRI(NEB, R0101S) and XhoI(NEB, R0146S), respectively.

The constructed vectors were amplified using a Qiagen Maxiprep kit (Cat No. 12662), and vectors including the heavy chain and vectors including the light chain were added to 293T cells ($2.5 \times 10^7$) at a ratio of about 4:1 (about 80 ug:20 ug) with 360 ul of 2 M $CaCl_2$ and were transfected. Next, the mixture was cultured in a DMEM medium with 10% FBS at 37° C. in 5% $CO_2$ conditions for 5 hours, and then cultured in a DMEM medium without FBS at 37° C. in 5% $CO_2$ conditions for 48 hours.

The cultured cells were centrifuged, and 100 ml of each supernatant was purified using AKTA Prime (GE healthcare). A Protein A column (GE healthcare, 17-0405-03) was placed in the AKTA Prime, and the cultured solution was flowed at a flow rate of 5 ml/min and was eluted with IgG elution buffer (Thermo Scientific, 21004). The buffer was exchanged with a PBS buffer, and thus 4 types of antibodies having improved affinity (hereinafter, huAbF46-H4-A1, huAbF46-H4-A2, huAbF46-H4-A3, and huAbF46-H4-A5) were purified.

(5) Analysis of Binding Affinity of Selected Antibodies

Affinities of the 4 types of antibodies against c-Met antigen were measured by using a Biacore (GE healthcare). About 80 to 110 RU of each antibody was immobilized on a CM5 chip, and 9 different concentrations ranging from 0.39 nM to 100 nM of human c-Met protein, as an antigen, were injected at a rate of 30 ul/min to obtain $k_{on}$ values and $k_{off}$ values as shown in Table 3. Then, $K_D$ values were calculated based thereon. A binding force of huAbF46 to c-Met antigen was about 2.19 nM, and binding forces of the four types of antibodies having improved affinity were in a range of 0.06 nM to 0.50 nM (Table 3). This indicates that affinities of the antibodies, which were improved in the form of scFv, were further improved by about 5 times to about 37 times after being transformed to IgG

TABLE 3

| Antibody | $k_{on}$ (1/Ms) | $k_{off}$(1/s) | $K_D$ ( nM ) |
|---|---|---|---|
| huAbF46 | $3.29 \times 10^5$ | $7.23 \times 10^{-4}$ | 2.19 |
| huAbF46-H4-A1 | $7.39 \times 10^5$ | $4.53 \times 10^{-5}$ | 0.06 |
| huAbF46-H4-A2 | $5.02 \times 10^5$ | $2.53 \times 10^{-4}$ | 0.50 |
| huAbF46-H4-A3 | $4.19 \times 10^5$ | $1.43 \times 10^{-4}$ | 0.34 |
| huAbF46-H4-A5 | $5.72 \times 10^5$ | $2.40 \times 10^{-4}$ | 0.42 |

Example 5

Confirm the Ability of Mouse Antibody AbF46 to Recognize c-Met (1) Confirm the Ability of Mouse Antibody AbF46 to Recognize Full Length c-Met To confirm the ability of mouse antibody AbF46 to recognize an extracellular domain of c-Met, a polynucleotide (SEQ ID NO: 57) encoding c-Met was cloned into a pcDNA5 vector (Invitrogen), and the resultant vector was expressed in a 293T cell (Korea Cell Line Bank) using an in vitro transcription and translation kit (TnTt kit, Promega, Madison, USA). Afterwards, mouse antibody AbF46 was mixed with protein G-conjugated agarose beads (Invitrogen), a 293T cell lysate including synthesized c-Met protein or c-Met produced by reaction from the in vitro transcription and translation kit was added to the mixture, and immunoprecipitation was then performed on the resultant mixture. The immunoprecipitated resultant was subjected to electrophoresis through SDS-PAGE and then analyzed by Western blotting.

Figure 2:
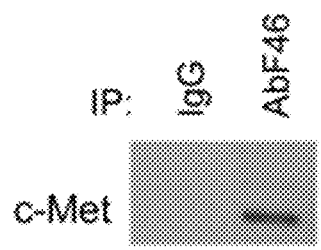
FIG. 2 is an image showing results of confirming recognition of mouse antibody AbF46 with respect to full-length c-Met, according to an embodiment.

As illustrated in FIG. 2, it was confirmed that mouse antibody AbF46 accurately recognized a full-length c-Met antigen.

(2) Confirm the Ability of Mouse Antibody AbF46 to Recognize a SEMA Domain

To confirm which region of the extracellular domain of c-Met mouse antibody AbF46 binds to, first, the extracellular domain of c-Met was divided into three regions, and a DNA fragment encoding each region was then cloned into a pcDNA5 vector. In this regard, the three regions were a SEMA domain (SEQ ID NO: 58), a PSI-IPT domain (SEQ ID NO: 59), and a TyrKc domain (SEQ ID NO: 60), and the DNA fragments encoding the three regions cloned into the pcDNA5 vector were represented by SEQ ID NO: 61, SEQ ID NO: 62, and SEQ ID NO: 63, respectively.

After each DNA fragment was cloned into the vector, each vector was expressed in a 293T cell (Korea Cell Line Bank) using an in vitro transcription and translation kit (TnTt kit, Promega, Madison, USA). Afterwards, mouse antibody AbF46 was mixed with protein G-conjugated agarose beads (Invitrogen), a 293T cell lysate including synthesized c-Met protein or c-Met produced by reaction from the in vitro transcription and translation kit was added to the mixture, and immunoprecipitation was then performed on the resultant mixture. The immunoprecipitated resultant was subjected to electrophoresis through SDS-PAGE and then analyzed by Western blotting.

Figure 3:
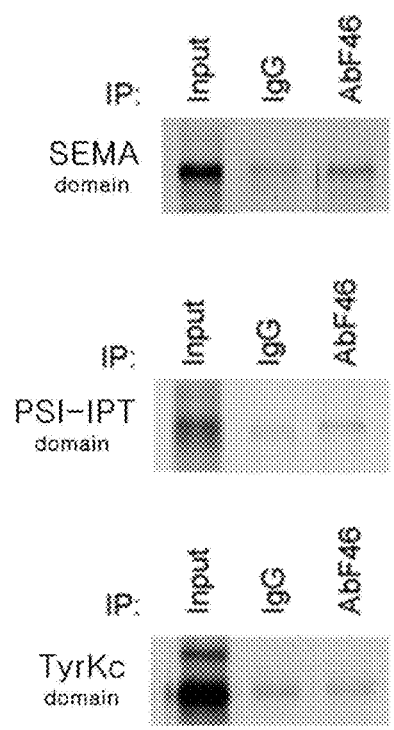
FIG. 3 is a set of images showing results of confirming recognition of mouse antibody AbF46 with respect to a SEMA domain, according to an embodiment.

As illustrated in FIG. 3, it was confirmed that mouse antibody AbF46 was bound to the SEMA domain of c-Met. Mouse IgG was used as a negative control, and a 5D5 antibody (isolated from a hybridoma cell with ATCC Cat. #HB11895 and purified) was used as a positive control. In FIG. 3, "Input" refers to all resulting materials synthesized without immunoprecipitation that were loaded on a gel. From the results, it is confirmed that all the synthesized c-Met proteins are intact regardless of whether they bind to the antibody.

Example 6

Analysis for Epitope of huAbF46

(1) Epitope Mapping

1) Preparation of Peptide for Epitope Mapping of huAbF46

543 amino acid sequences, including the SEMA domain of c-Met and structures thereof, are represented in PDB (Protein Database) ID: 1UZY, and 6,063 other sequences capable of producing a conformational epitope and a discontinuous epitope were designed and synthesized based on the 543 amino acid sequences by using a Chemically Linked Peptides on Scaffolds (CLIPS) technology (Timmerman et al., Functional reconstruction and synthetic mimicry of a conformational epitope using CLIPS™ technology. *J. Mol. Recognit.*, 20: 283-300 (2007)). The peptide array fabrication will now be described in more detail. The CLIPS technology developed by PepScan is used to prepare peptides having an intrinsic structure called CLIPS rather than linear peptides having a length of about 15 amino acids, prepared using a known typical method. The binding affinity of huAbF46 with the linear peptides and the CLIPS peptides was measured. Among the CLIPS peptides, T2 CLIPS peptides are prepared such that two cysteines are linked together to form a loop so that the peptides have an artificial structure, and T3 CLIPS peptides are prepared such that three cysteines are linked together to form a loop so that the peptides have an artificial structure. In addition, binding-type peptides such as T2T3 or T2T2 CLIPS peptides may be prepared.

A total number of 6,063 peptides were prepared for epitope mapping (peptide array design was applied to PepScan). In this regard, $1^{st}$ through $529^{th}$ peptides, which are typical linear peptides, were prepared such that the peptides had a length of 15 amino acids and an overlapped region between certain regions. $530^{th}$ through $1,058^{th}$ peptides were prepared by introducing $1^{st}$ through $529^{th}$ peptides to T2 CLIPS peptides. $1,059^{th}$ through $2,014^{th}$ peptides, i.e., a total number of 956 peptides, were prepared by linking two peptides each having 15 amino acids to T3 CLIPS peptides. $2,015^{th}$ through $6,063^{rd}$, i.e., a total number of 4,048 peptides, were prepared as peptides for searching epitopes having conformational and discontinuous structures through binding between peptide groups having 8 to 35 amino acid residues.

For example, a peptide array including T2 CLIPS peptides was prepared as follows. 0.5 mM of a 1,3-bis(bromomethyl) benzene solution including T2 CLIPS peptides was dissolved in ammonium bicarbonate (20 mM, pH 7.9)/acetonitrile (1:1 (v/v), and the resultant solution was added to a peptide array. The T2 CLIPS peptides as a template were bound to two cysteine side chains existing in a solid-phase bound peptide of the peptide array (455-well plate having 3 ul of wells). The peptide array was slowly shaken in the solution for 30 to 60 minutes. Lastly, the peptide array was sufficiently washed with a large amount of water, was ultrasonically fragmented in a lysate-buffer containing 1% SDS/0.1% beta-mercaptoethanol in PBS (pH 7.2) at 70° C. for 30 minutes, and further ultrasonically fragmented in water for 45 minutes. T3 CLIPS peptides were prepared using the same method as described above, except that the T3 CLIPS peptides as a template were bound to three cysteine side chains.

As a result of performing epitope mapping by using the peptides by ELISA, a core epitope of huAbF46 was confirmed to be EEPSQ (SEQ ID NO: 3) a peptide consisting of the $168^{th}$ through $171^{th}$ amino acids of c-Met protein.

2) ELISA for Epitope Mapping of huAbF46

For epitope mapping, PEPSCAN-based ELISA was performed using a total number of 529 linear and CLIPS peptides. The peptides were maintained at room temperature for 30 minutes by using a 5% blocking solution to provoke a reaction (4% ovalbumin, 5% horse serum, and 1% Tween 80). Then, 1 to 100 ug/ml of huAbF46 antibody, maintained in PBS containing 1% Tween 80 at 4° C. overnight, was reacted with the peptides and the resultant product was then washed. Thereafter, the resultant product was treated with rabbit-anti-sheep antibody (SIGMA) and washed with PBS, and the washed product was then treated with peroxidase-attached swine-anti-rabbit antibody (SIGMA) and washed with PBS. Then, the resultant product was treated with 2 ul/ml of peroxidase 2,2'-azino-di-3-ethylbenzthiazoline sulfonate (ABTS)(SIGMA) in 3% $H_2O_2$, and a color reaction was measured after 1 hour.

Figure 4:
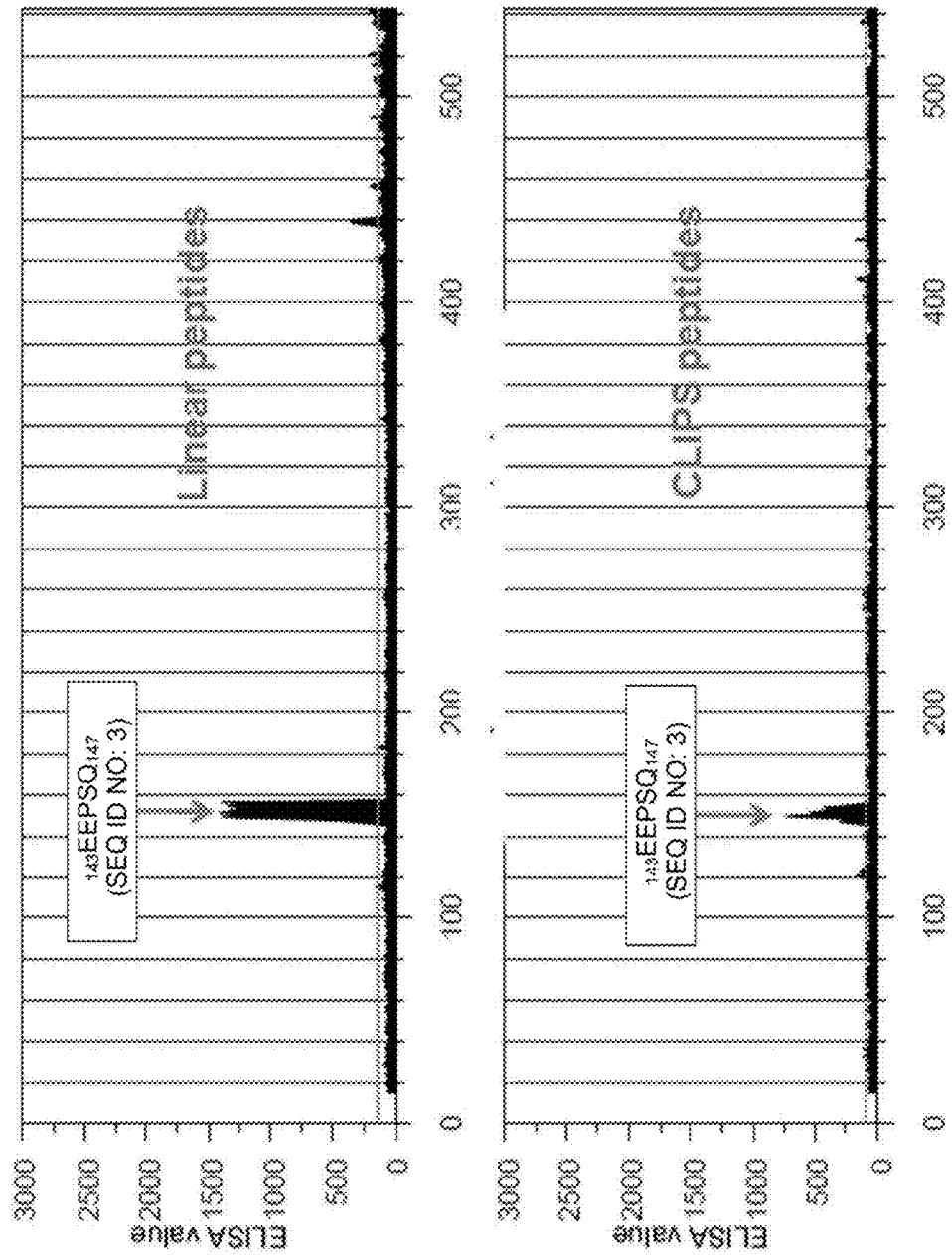
FIG. 4 is a set of graphs showing enzyme-linked immunosorbent assay (ELISA) results for epitope mapping of huAbF46, according to an embodiment.
Figure 5:
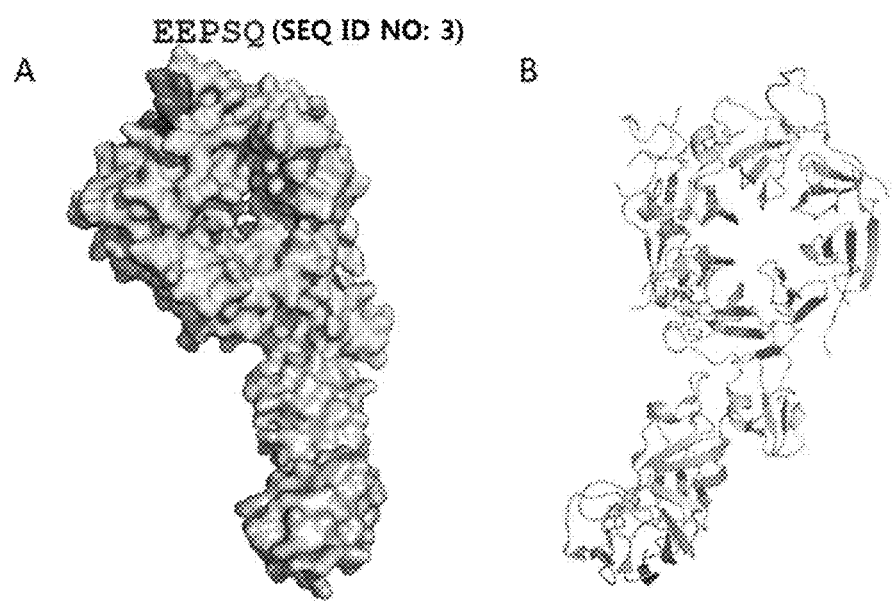
FIGS. 5A and 5B are images confirming a position of an epitope of huAbF46 on a SEMA domain, according to an embodiment.

As a result, as illustrated in FIG. 4, only the peptides including EEPSQ (SEQ ID NO: 3) of both the linear peptides and the CLIPS peptides exhibited a specific ELISA positive reaction, and thus the huAbF46 antibody was confirmed to recognize the linear and conformational epitopes of c-Met.

In addition, an ELISA was performed in the same manner as described above by using polypeptides with E168D mutation, which is a representative SEMA domain mutation of c-Met known to be found in some patients with lung cancer or ovarian cancer, among the epitopes including the peptides including EEPSQ (SEQ ID NO: 3). The results are shown in Table 4 below.

TABLE 4

| Core peptide sequence | Synthesized peptide sequence | ELISA value (antibody binding of huAbF46) |
|---|---|---|
| EEPSQ (SEQ ID NO: 3) | FAPQIEEPSQCPDCVVSALGAKVL (SEQ ID NO: 64) | 2063 |
| | CSPQIEEPSQC (SEQ ID NO: 65) | 1306 |
| | CPQIEEPSQAC (SEQ ID NO: 66) | 2157 |

TABLE 4-continued

| Core peptide sequence | Synthesized peptide sequence | ELISA value (antibody binding of huAbF46) |
|---|---|---|
| | CQIEEPSQAPC (SEQ ID NO: 67) | 2744 |
| | CIEEPSQAPDC (SEQ ID NO: 68) | 2239 |
| | CEEPSQAPDAC (SEQ ID NO: 69) | 2829 |
| EDPSQ (SEQ ID NO: 70) | FSPQIEDPSQCPDCVVSALGAKVL (SEQ ID NO: 71) | 172 |
| | CSPQIEDPSQC (SEQ ID NO: 72) | 121 |
| | CPQIEDPSQAC (SEQ ID NO: 73) | 138 |
| | CQIEDPSQAPC (SEQ ID NO: 74) | 172 |
| | CIEDPSQAPDC (SEQ ID NO: 75) | 128 |
| | CEDPSQAPDAC (SEQ ID NO: 76) | 132 |

From the above results, it was confirmed that the huAbF46 antibodies were not able to bind to the SEMA domain of c-Met with the E168D mutation. This indicates that the antibodies may be used in a diagnosis method for providing cancer development information.

3) Analysis of Epitope Mapping Results of huAbF46

From the results shown above, it was confirmed that the huAbF46 antibodies specifically bound to both the linear and CLIPS peptides including the EEPSQ (SEQ ID NO: 3) peptides consisting of $168^{th}$ to $171^{th}$ amino acids of c-Met protein without a non-specific reaction. This indicates that the huAbF46 antibodies bind to both the linear and conformational epitopes of c-Met protein. In terms of molecular structures (PyMOL 1.4.1), Cn3D 4.1 (NCBI)), as illustrated in FIG. 5, it was confirmed that an epitope of huAbF46 was located at a SEMA domain. In addition, it was confirmed that a binding site of HGF was a position corresponding to a loop close to a direct binding site.

(2) Analysis of Full Positional Scanning Results

Each amino acid region of the EEPSQ (SEQ ID NO: 3) sequence was substituted with 20 amino acids rather than the original amino acids, and any change that occurred in the binding affinity between each peptide and huAbF46 antibody was analyzed through 7 peptide arrays.

As a result of the analysis, it was confirmed which amino acid of the amino acid sequences of the EEPSQ (SEQ ID NO: 3) sequence played a key role in binding with the antibody. In particular, it was confirmed that the EEP sequence in EEPSQ (SEQ ID NO: 3) played a very critical role in binding with the antibody.

Example 7

Analysis of Binding Affinity of huAbF46 Antibody by SEMA Domain Mutation

Each amino acid region or the total number of 5 amino acids of the EEPSQ (SEQ ID NO: 3) sequence was substituted with alanine rather than the original amino acid, and a binding affinity between each peptide ('AAAAA' (SEQ ID NO: 77), 'AEPSQ' (SEQ ID NO: 78), 'EAPSQ' (SEQ ID NO: 79), 'EEASQ' (SEQ ID NO: 80), 'EEPAQ' (SEQ ID NO: 81), 'EEPSA' (SEQ ID NO: 82)) and the huAbF46 antibody was measured using Biacore (GE healthcare). About 80 to 110 RU of the huAbF46 antibody was immobilized on a CM5 chip, and 100 nM to 0.39 nM of the peptides having amino acid sequences of SEQ ID NOs: 77 through 82 were injected thereto at a rate of 30 ul/min in 9 different concentrations, thereby obtaining $k_{on}$ and $k_{off}$ values as shown in Table 5 below, and $K_D$ values were calculated therefrom. As a result, it was confirmed that the huAbF46 antibodies were not able to bind to the peptides with the substituted amino acids. From this result, the EEPSQ (SEQ ID NO: 3) sequence was confirmed to be an essential epitope of the huAbF46 antibody.

TABLE 5

| Antibody | Antigen | $k_{off}$(1/Ms) | $k_{on}$(1/s) | $K_D$ (nM) |
|---|---|---|---|---|
| huAbF46 | EEPSQ (SEQ ID NO: 3) | $4.30 \times 10^5$ | $7.05 \times 10^{-4}$ | 1.64 |
| huAbF46 | AAAAA (SEQ ID NO: 77) | | Not bound | |
| huAbF46 | AEPSQ (SEQ ID NO: 78) | | Not bound | |
| huAbF46 | EAPSQ (SEQ ID NO: 79) | | Not bound | |
| huAbF46 | EEASQ (SEQ ID NO: 80) | | Not bound | |
| huAbF46 | EEPAQ (SEQ ID NO: 81) | $4.32 \times 10^5$ | $6.16 \times 10^{-4}$ | 1.43 |
| huAbF46 | EEPSA (SEQ ID NO: 82) | | Not bound | |

Example 8

Comparison of Agonism Dysfunction Degree of huAbF46 Antibody

BrdU Assay

To compare a degree of agonism against a huAbF46 antibody, a BrdU assay was performed using NCI-H441 cells. The NCI-H441 cells, which are human lung cancer cells, were suspended in a RPMI 1640 medium (Gibco) at a concentration of $2\times10^5$ cells/ml and 100 ul of the suspension was distributed to each well of a 96-well tissue culture plate (Corning, Lowell, Mass.). The cells were cultured at 37° C. in 5% $CO_2$ conditions for 24 hours, and a diluted RPMI 1640 medium was added to the antibodies after the medium was completely removed. The cells were cultured at 37° C. in 5% $CO_2$ conditions for 21 hours, 5-bromo-2'-deoxyuridine (BrdU) was added thereto, the cells were further cultured for 3 hours, and a BrdU assay (Roche, Indianapolis, Ind.) was performed thereon. The cells were subjected to denaturation/fixation on a plate, anti-BrdU antibodies were added thereto, a substrate was added 1 hour thereafter, and a color reaction was measured using an ELISA spectraMax reader (Molecular Devices, Sunnyvale, Calif.). In this regard, the agonism of mouse antibody AbF46 was compared with the agonism of huAbF46 antibody. Mouse IgG was used as a negative control and a 5D5 antibody known to be an agonist was used as a positive control.

Figure 6A:
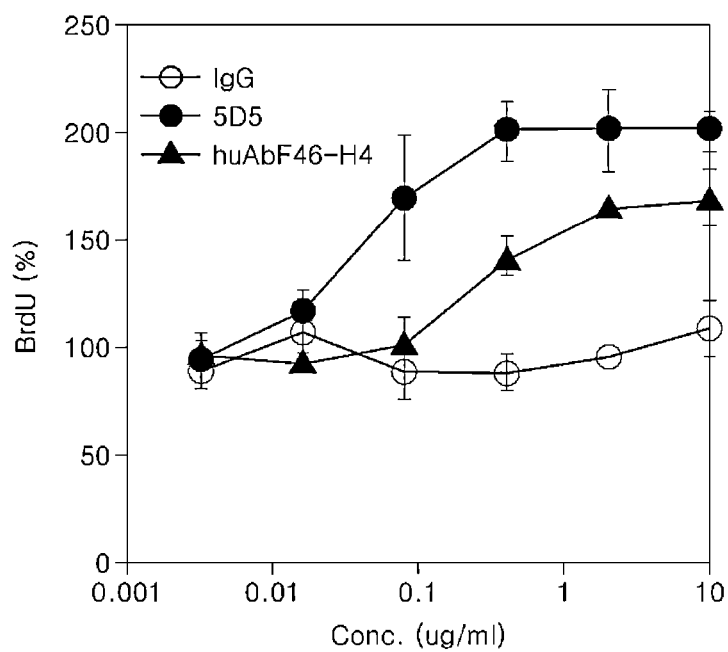
FIGS. 6A and 6B are graphs showing results of confirming a degree of agonism of humanized antibody huAbF46 by BrdU assay, according to an embodiment.
Figure 6B:
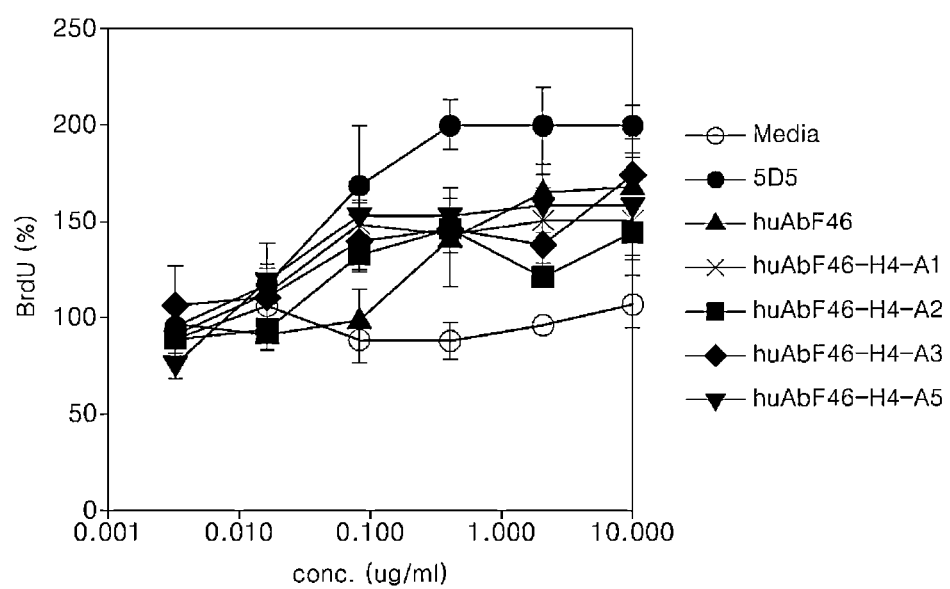

As illustrated in FIG. 6A, it was confirmed that the huAbF46 antibody reduced a degree of agonism dysfunction, similar to that of the 5D5 antibody. In addition, referring to FIG. 6B, among the 4 types of antibodies having improved affinity, agonism side effects of 3 types were reduced. Thus, it was identified that safeties thereof were respectively improved by 25% (huAbF46-H4-A1), 28% (huAbF46-H4-A2), 13% (huAbF46-H4-A3), and 21% (huAbF46-H4-A5) at a concentration of 10 ug/ml.

(2) In Vitro Cell Proliferation Analysis

In order to identify anti-cancer effects of the 4 types of antibodies having improved affinity, in vitro cell proliferation analysis was performed using MKN45 gastric cancer cells on which c-Met is expressed (Japanese Cancer Research Bank, JCRB, Tokyo, Japan).

$1 \times 10^4$ MKN45 cells suspended in 50 ul of 5% FBS/DMEM culture medium were introduced to each well of a 96-well plate. Then, the cells were either not treated or treated with 50 ul of the 4 types of antibodies at a concentration of 0.008, 0.04, 0.2, or 1 ug/ml. After incubating for 72 hours, the number of cells were quantified by using a CellTiter-Glo Luminescent Cell Viability Assay Kit (Promega, G7570) with a leuminometer (PerkinElmer, 2104 Multilabel reader).

Figure 7:
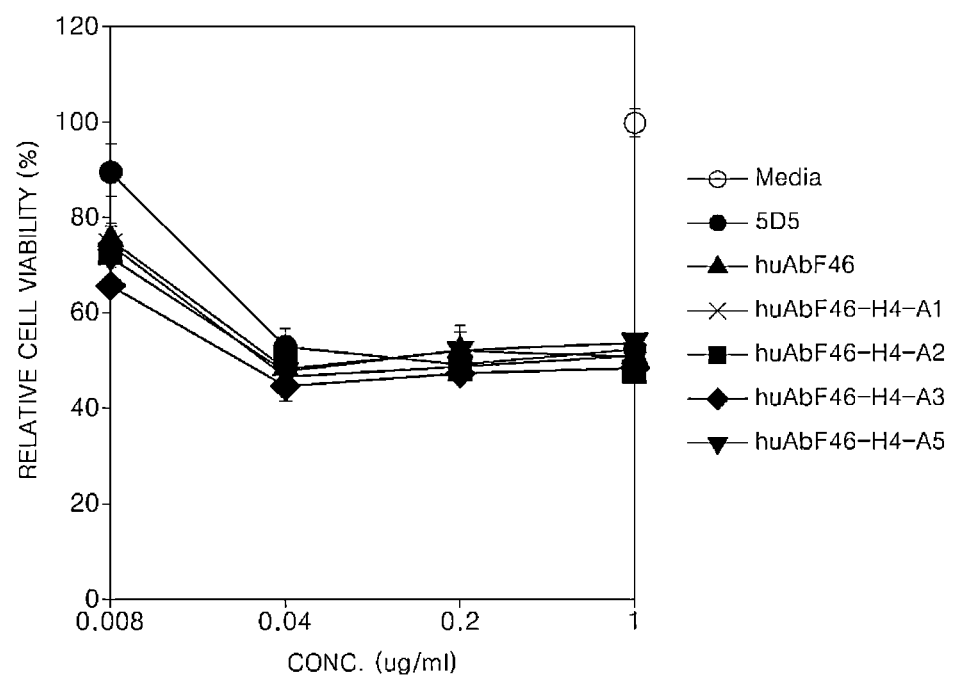
FIG. 7 is a graph illustrating results of in vitro cell viability of huAbF46-H4-A1, huAbF46-H4-A2, huAbF46-H4-A3, and huAbF46-H4-A5 antibodies according to an embodiment.

As shown in FIG. 7, relative cell viability of the antibody (huAbF46) in which the affinity was not improved was 77% at the lowest concentration of 0.008 ug/ml, and relative cell viabilities of antibodies having improved affinity, i.e., huAbF46-H4-A1, huAbF46-H4-A2, and huAbF46-H4-A5 were respectively 74, 73, and 72% similar to each other. The relative cell viability of huAbF46-H4-A3, as 66%, was considerably increased. In addition, at 0.04 ug/ml where the viability are maximized, relative cell viabilities of all of the 4 types of antibodies were less than 53% that is viability of the 5D5 antibody. Accordingly, it was identified that, as a result of improving affinity, efficiency and safety were significantly improved compared to the control group.

(3) Akt Phosphorylation

To compare a degree of agonism against a huAbF46 antibody, a phosphorylation degree of Akt protein, which is an indicator involved in downstream signal transduction and cell proliferation of c-Met, was confirmed using Caki-1 cells (Korea Cell Line Bank). Mouse IgG was used as a negative control and a 5D5 antibody known to be an agonist was used as a positive control.

$2 \times 10^5$ cells/ml of the Caki-1 cell was distributed to each well of a 96-well plate, and, after 24 hours, 5 ug/ml of an antibody was treated with the cells of each well in a serum-free state for 30 minutes. The cells treated with the antibodies were lysed, and a phosphorylation degree of Akt protein was measured using PathScan phospho-AKT1 (Ser473) chemiluminescent Sandwich ELISA kit (Cell Signaling, cat. no #7134S) and analyzed.

Figure 8A:
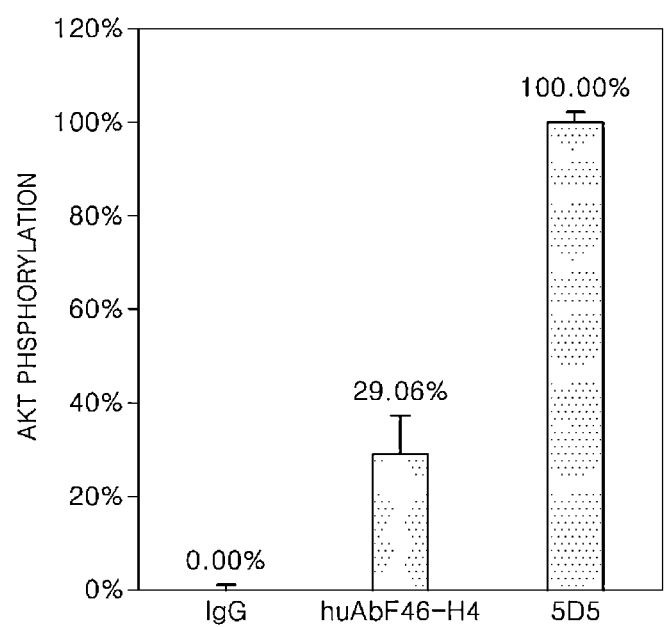
FIGS. 8A and 8B are graphs showing results of confirming a degree of agonism of humanized antibody huAbF46 by Akt phosphorylation, according to an embodiment.
Figure 8B:
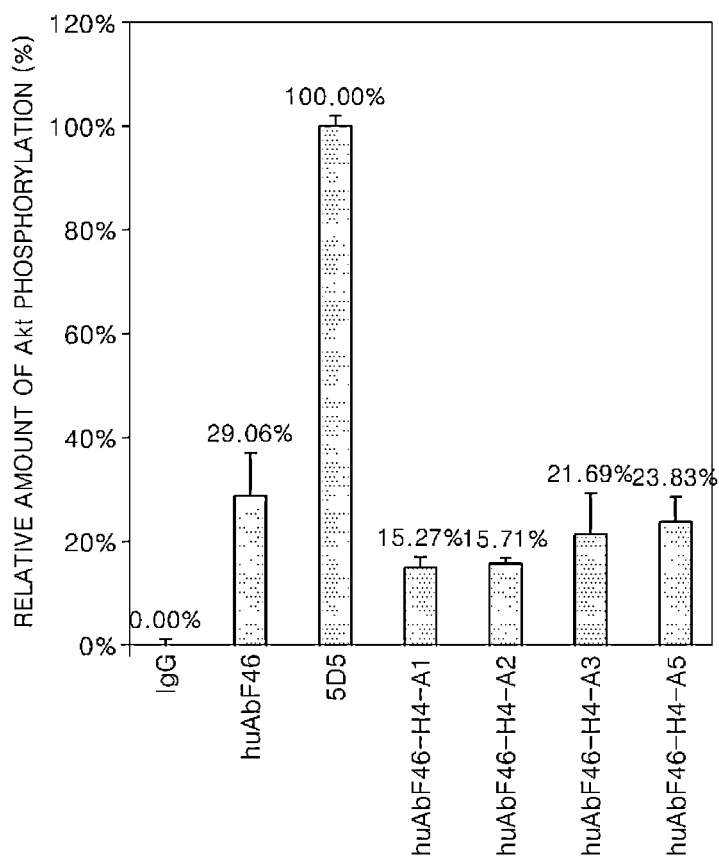

As illustrated in FIGS. 8A and 8B, the phosphorylation degree of Akt protein in a case in which the huAbF46 antibody was treated was confirmed to be less than 30%. From the results, it was confirmed that the huAbF46 antibody had reduced agonism dysfunction.

(4) Identification of Degree of Degradation of c-Met

In order to identify anti-cancer effects of the 4 types of antibodies having improved affinity, the degree of degradation of c-Met bound to the antibody was evaluated. A relative total amount of c-Met was obtained by measuring the change of the total amount of c-Met after the antibody bound to c-Met to degrade c-Met via internalization, and thus efficacy of the antibody was evaluated.

MKN45 cells ($2 \times 10^5$ cells/ml) and each of the 4 types of antibodies (5 ug/ml) were simultaneously introduced to a 96-well plate and incubated for 24 hours. Then, lysis of the cells treated with antibodies was performed and a change of the total amount of c-Met was measured using a Human total HGF R/c-MET ELISA KIT (R&D systems, DYC358) and analyzed.

Figure 9:
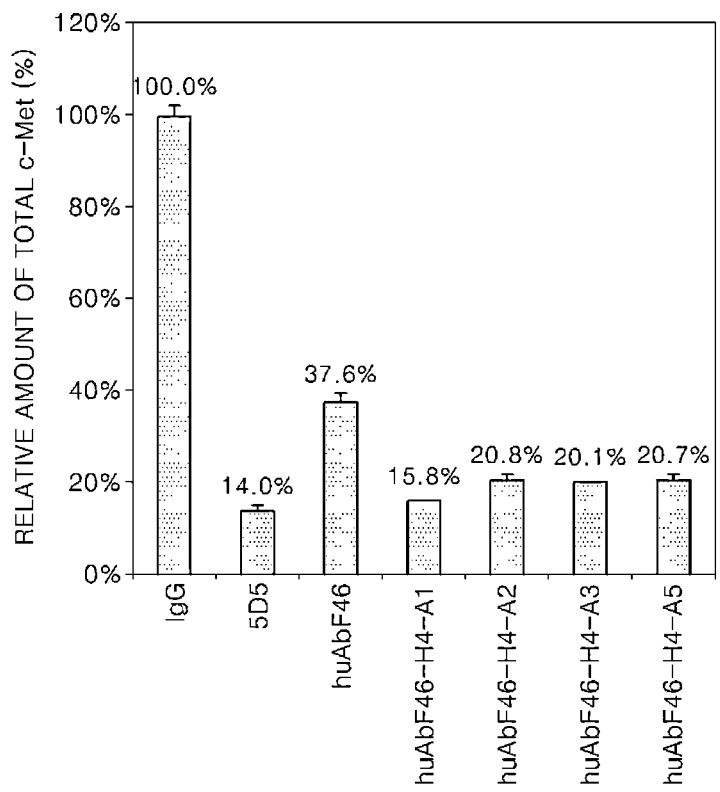
FIG. 9 is a graph illustrating anti-cancer effects of huAbF46-H4-A1, huAbF46-H4-A2, huAbF46-H4-A3, and huAbF46-H4-A5 antibodies according to an embodiment by measuring degrees of degradation of c-Met.

As a result, referring to FIG. 9, it was identified that the degree of degradation of c-Met was improved when treated with the 4 types of antibodies having improved affinity compared to the huAbF46 antibody. The degree of degradation of c-Met treated with huAbF46-H4-A1 was increased by about 37% compared to huAbF46. The degrees of degradation of c-Met treated with huAbF46-H4-A2, huAbF46-H4-A3, and huAbF46-H4-A5 were increased by about 28% compared to huAbF46.

Example 9

Analysis of In Vitro Anti-Cancer Effect of huAbF46 Antibody

To confirm anti-cancer effects of the humanized antibody huAbF46 by inhibiting proliferation of cancer cells, in vitro cell proliferation analysis was performed using MKN45 stomach cancer cells expressing c-Met molecules on their surfaces (Japanese Cancer Research Bank, JCRB, Tokyo, Japan).

$1 \times 10^4$ of MKN45 cells were distributed into each well of a 96-well plate together with 50 ul of a 5% FBS/DMEM culture, and the cells were either not treated with huAbF46 antibody or were treated with 0.008, 0.04, 0.2 or 1 ug/ml of the huAbF46 antibody. The treated cells were cultured for 72 hours, and the number of the cultured cells were counted using a leuminometer (PerkinElmer, 2104 Multilabel reader) by using CellTiter-Glo® Luminescent Cell Viability Assay Kit (Promega, G7570).

Figure 10:
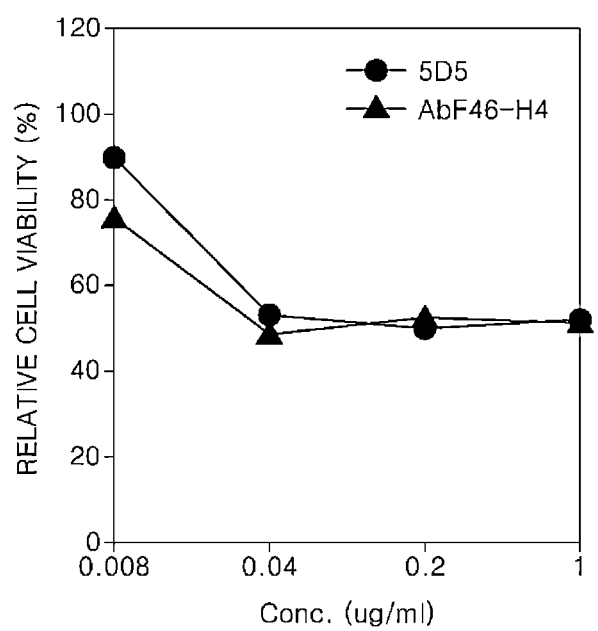
FIG. 10 is a graph showing in vitro cell viability analysis results of humanized antibody huAbF46, according to an embodiment.

As illustrated in FIG. 10, it was confirmed that while the mouse IgG used as a negative control did not inhibit proliferation of cancer cells, the huAbF46 antibody did inhibit proliferation of cancer cells.

Example 10

Confirmation of In Vivo Anti-Cancer Effects of Mouse Antibody AbF46, chAbF46 and huAbF46

To confirm the anti-cancer effects of the mouse antibody AbF46, the chimeric antibody chAbF46, and the humanized antibody huAbF46 prepared according to the Examples above, it was evaluated whether sizes of tumors were reduced by administration of these antibodies in vivo using a mouse xenograft model administered with U87MG brain cancer cells (Korean Cell Line Bank), stomach cancer cell lines MKN45 Japanese Cancer Research Bank, JCRB, Tokyo, Japan) or lung cancer cell lines NCI-H441 (ATCC Cat. #HTB-174). Each of the three types of antibodies have the same complimentarity determining region (CDR) and, thus, are expected to bind to the same epitope of c-Met.

The mouse xenograft model was produced such that 50 ul of U87MG brain cancer cells, stomach cancer cells MKN45, or lung cancer cells NCI-H441 ($3 \times 10^6$ cells/50 ul) was administered via subcutaneous injection to 6-week-old male BALB/C nude mice (available from ORIENT BIO Inc.). 12 mice per group that contracted cancer were randomly selected, and the produced model was used in the experiment. 10 mg/kg of the three antibodies was administered via intravenous injection to the mice once a week after formation of cancer cells. In addition, as a control, 10 mg/kg and 20 mg/kg of the mouse antibody AbF46 were administered via intraperitoneal injection to the mouse model twice a week.

Figure 11A:
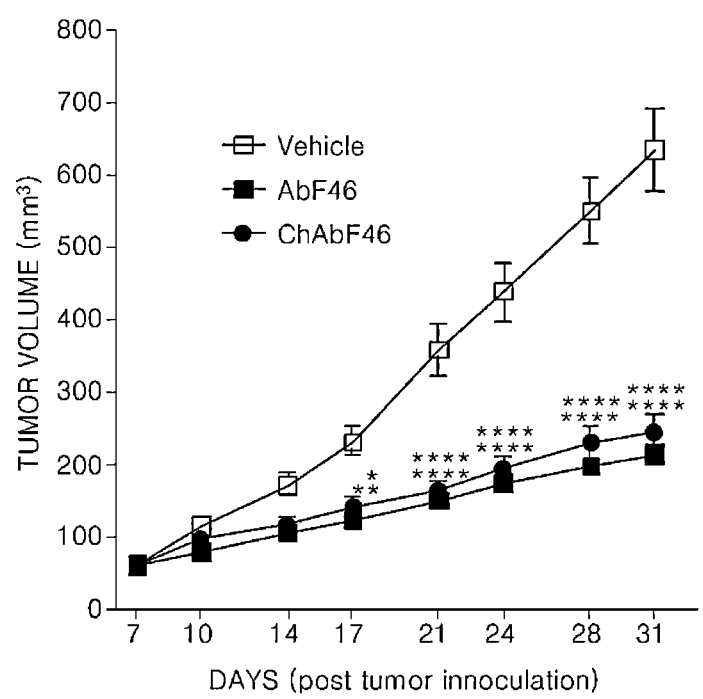
FIGS. 11A to 11C are graphs showing results of analyzing in vivo anti-cancer effects of mouse antibody AbF46 and chimeric antibody chAbF46 by using a mouse brain cancer xenograft model or stomach cancer xenograft model, according to an embodiment.
Figure 11B:
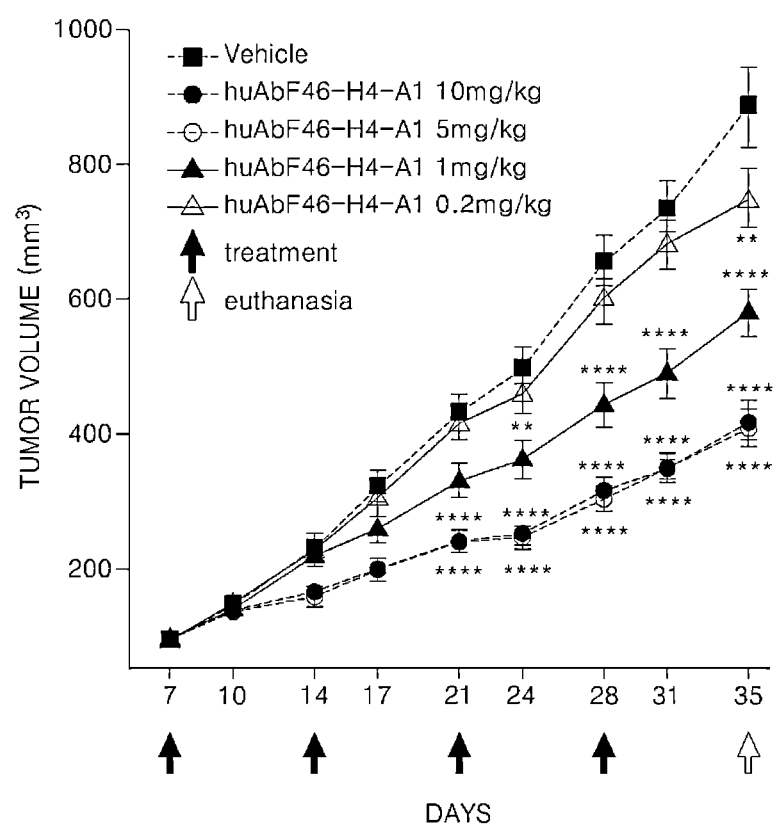
Figure 11C:
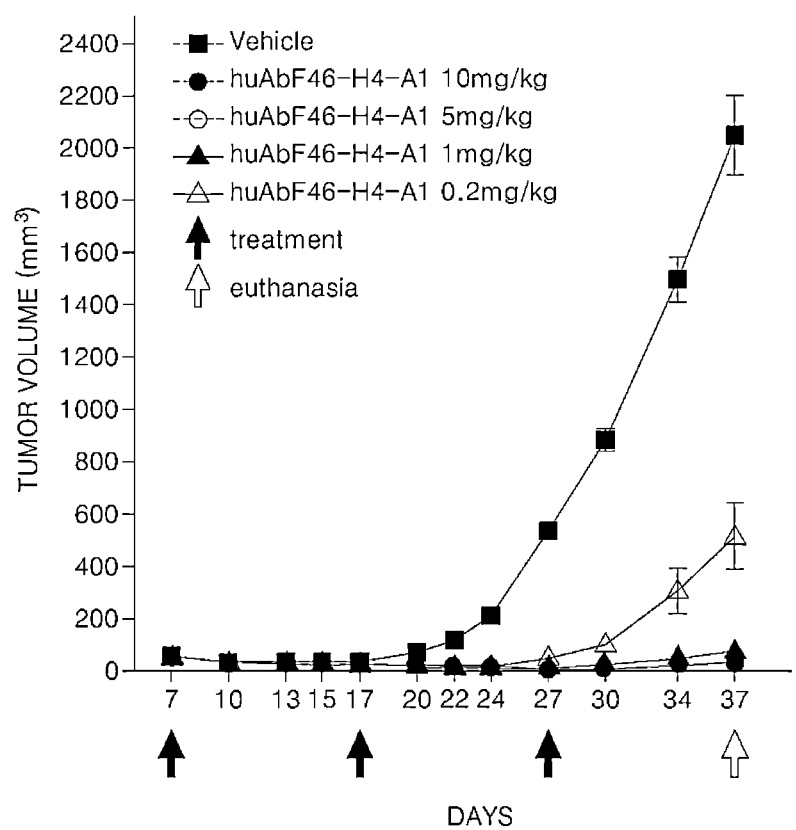

As illustrated in FIGS. 11A to 11C, as a result of measuring sizes of tumors over time in the mouse xenograft group (U87MG brain cancer cells, stomach cancer cells MKN45), it was confirmed that the mouse antibody AbF46 and the chimeric antibody chAbF46 had significant anti-cancer effects. In this regard, the number of mice per group in an experimental group (mouse antibody AbF46 and chAbF46) and a control (vehicle) was 12, and an average and SEM of each group were represented. In FIGS. 11A to 11C, p-values obtained by comparing the two experimental groups and the control by using repeated measures ANOVA were represented by * (*: $p<0.05$, : $p<0.01$, **: $p<0.0001$).

Figure 12:
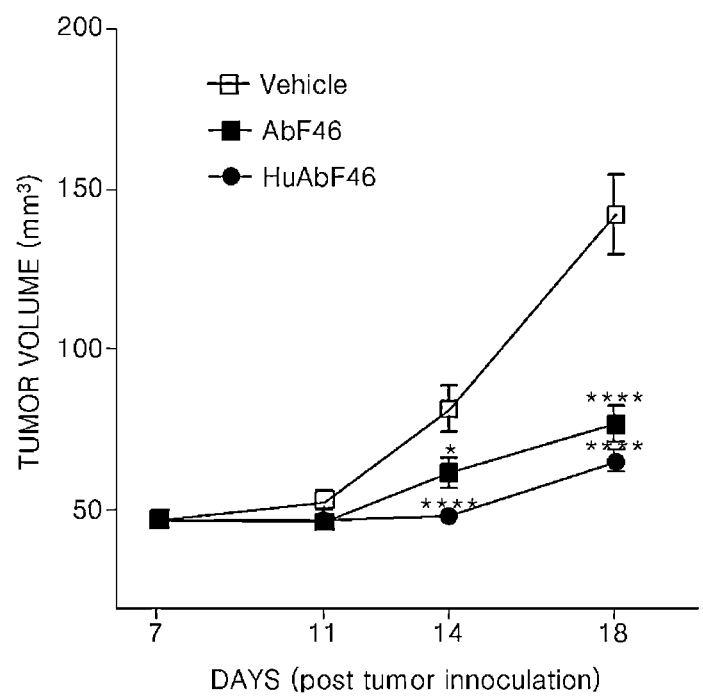
FIG. 12 is a graph showing results of analyzing in vivo anti-cancer effects of mouse antibody AbF46 and humanized antibody huAbF46 by using a mouse lung cancer xenograft model, according to an embodiment.

In addition, as illustrated in FIG. 12, as a result of measuring sizes of tumors over time in the mouse xenograft model (lung cancer cells NCI-H441), it was confirmed that the mouse antibody AbF46 and the humanized antibody huAbF46 had significant anti-cancer effects. In this regard, the number of mice per group in an experimental group (mouse antibodies AbF46 and chAbF46) and a control (vehicle) was 15, and an average and SEM of each group were represented. In FIG. 12, p-values obtained by comparing the two experimental groups and the control by using repeated measures ANOVA were represented by * (*: $p<0.05$, ****: $p<0.0001$).

As described above, according to the one or more of the above embodiments of the present invention, there is provided an antibody that specifically binds to an epitope in a SEMA domain of c-Met and a pharmaceutical composition for preventing or treating cancer that includes the antibody, whereby cancer may be efficiently prevented or treated.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. An antibody or antigen binding fragment thereof that specifically binds to an epitope in a SEMA domain of c-Met protein, wherein the epitope consists of SEQ ID NO: 3 or a portion of SEQ ID NO: 1 that includes SEQ ID NO: 3, wherein the antibody or antigen binding fragment thereof does not comprise the same complementarity determining regions (CDRs) as an antibody produced by hybridoma KCLRF-BP-00200.

2. The antibody or antigen binding fragment thereof of claim 1, wherein the antibody or antigen binding fragment thereof is a monoclonal antibody, bispecific antibody, multi-specific antibody or antigen binding fragment selected from the group consisting of scFv, (scFv)2, Fab, Fab', and F(ab')2.

3. The antibody or antigen binding fragment thereof of claim 1, wherein the antibody or antigen binding fragment thereof specifically binds human c-Met protein.

4. The antibody or antigen binding fragment thereof of claim 1, wherein the antibody or antigen binding fragment thereof is an antagonist of c-Met protein.

5. The antibody or antigen binding fragment thereof of claim 1, wherein the antibody or antigen binding fragment thereof is synthetic or recombinant.

6. A pharmaceutical composition comprising a therapeutically effective amount of the antibody or antigen binding fragment thereof of claim 1 and a pharmaceutically acceptable carrier, diluent, or excipient.

7. A method of treating a cancer characterized by c-Met expression in a human subject, the method comprising administering to the human subject the antibody or antigen binding fragment of claim 1, or a pharmaceutical composition comprising the antibody or antigen binding fragment of claim 1 and a pharmaceutically acceptable carrier, a diluent, or an excipient.

8. The method of claim 7, wherein the cancer is lung cancer, gastrointestinal cancer, or glioblastoma.

* * * * *